United States Patent
Weiss et al.

(10) Patent No.: US 7,164,008 B2
(45) Date of Patent: Jan. 16, 2007

(54) ISOLATED COMPLEXES OF ENDOTOXIN AND MD-2

(75) Inventors: Jerrold P. Weiss, Coralville, IA (US); Theresa L. Gioannini, Coralville, IA (US); Athamane Teghanemt, Coralville, IA (US); Ramaswamy Subramanian, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 143 days.

(21) Appl. No.: 10/715,876

(22) Filed: Nov. 17, 2003

(65) Prior Publication Data

US 2005/0106179 A1    May 19, 2005

(51) Int. Cl.
*A61K 39/02* (2006.01)
*C07K 14/195* (2006.01)

(52) U.S. Cl. .................... 530/395; 514/2; 424/35.1
(58) Field of Classification Search ............. 514/2
See application file for complete search history.

(56) References Cited

U.S. PATENT DOCUMENTS

| | | | |
|---|---|---|---|
| 3,561,444 A | 2/1971 | Boucher | |
| 3,703,173 A | 11/1972 | Dixon | |
| 4,624,251 A | 11/1986 | Miller | |
| 4,635,627 A | 1/1987 | Gam | |
| 4,962,091 A | 10/1990 | Eppstein et al. | |
| 2002/0192217 A1* | 12/2002 | Calandra et al. | 424/145.1 |
| 2003/0119720 A1* | 6/2003 | Khan et al. | 514/2 |
| 2003/0175762 A1* | 9/2003 | Nunez et al. | 435/6 |
| 2003/0232352 A1* | 12/2003 | Schwartz et al. | 435/6 |

FOREIGN PATENT DOCUMENTS

| | | |
|---|---|---|
| JP | 2003319734 | 11/2003 |
| WO | WO 94/07529 | 4/1994 |
| WO | WO 97/19688 | 6/1997 |

OTHER PUBLICATIONS

Viriyakosol et al. MD-2 binds to bacterial lipopolysaccharide. J Biol Chem. Oct. 12, 2001;276(41):38044-51. Epub Aug. 10, 2001.*
Abreu et al., "TLR4 and MD-2 Expression Is Regulated by Immune-mediated Signals in Human Intestinal Epithelial Cells," *J. Biol. Chem.*, 2002, 277(23):20431-20437.
Abreu et al., "Decreased Expression of Toll-Like Receptor-4 and MD-2 Correlates with Intestinal Epithelial Cell Protection Against Dysregulated Proinflammatory Gene Expression in Response to Bacterial Lipopolysaccharide," *J. Immunol.*, 2001, 167:1609-1617.
Akashi et al., "Lipopolysaccharide Interaction with Cell Surface Toll-like Receptor 4-MD-2: Higher Affinity than That with MD-2 or CD14," *J. Exp. Med.*, 2003, 198(7):1035-1042.
Akashi et al., "Cutting Edge: Cell Surface Expression and Lipopolysaccharide Signaling Via the Toll-Like Receptor 4-MD-2 Complex on Mouse Peritoneal Macrophages," *J. Immunol.*, 2000, 164:3471-3475.
Altschul et al., "Basic Local Alignment Search Tool," *J. Mol. Biol.*, 1990, 215:403-410.
Altschul et al., "Gapped BLAST and PSI-BLAST: a new generation of protein database search programs," *Nucl. Acids Res.*, 1997, 25(17):3389-3402.
Anderson et al., "A simple method for the rapid generation of recombinant adenovirus vectors," *Gene Ther.*, 2000, 7:1034-1038.
Anderson, "Toll signaling pathways in the innate immune response," *Curr. Opin. Immunol.*, 2000, 12:13-19.
Arbour et al., "TLR4 mutations are associated with endotoxin hyporesponsiveness in humans," *Nat. Genet.*, 2000, 25:187-191.
Bacchi et al., "Polyamine metabolism in the Microsporidia," *Biochemical Society Transactions*, 2003, 31(2):420-423.
Bals et al., "Human β-Defensin 2 Is a Salt-sensitive Peptide Antibiotic Expressed in Human Lung," *J. Clin. Invest.*, 1998, 102(5):874-880.
Bandi et al., "Nontypeable *Haemophilus influenzae* in the Lower Respiratory Tract of Patients with Chronic Bronchitis," *Am. J. Respir. Crit. Care Med.*, 2001, 164:2114-2119.
Becker et al., "CD14-dependent Lipopolysaccharide-induced β-Defensin-2 Expression in Human Tracheobronchial Epithelium," *J. Biol. Chem.*, 2000, 275(38):29731-29736.
Beutler and Poltorak, "Sepsis and evolution of the innate immune response," *Crit. Care Med.*, 2001, 29(7)(Suppl.):S2-S7.
Beutler and Rietschel, "Innate immune sensing and its roots: the story of endotoxin," *Nat. Rev. Immunol.*, 2003, 3:169-176.
Bustin "Absolute quantification of mRNA using real-time reverse transcription polymerase chain reaction assays," *J. Mol. Endocrinol.*, 2000, 25:169-193.

(Continued)

Primary Examiner—Christopher R. Tate
Assistant Examiner—Maury Audet
(74) Attorney, Agent, or Firm—Viksnins Harris & Padys PLLP

(57) ABSTRACT

Applicants have produced and isolated water soluble complexes of endotoxin and MD-2.

24 Claims, 14 Drawing Sheets

OTHER PUBLICATIONS

Corpet, "Multiple sequence alignment with hierarchical clustering," *Nucl. Acids Res.*, 1988, 16(22):10881-10890.

Correia et al., "Lipopolysaccharide Is in Close Proximity to Each of the Proteins in Its Membrane Receptor Complex," *J. Biol. Chem.*, 2001, 276(24):21129-21135.

Denning et al., "*Pseudomonas* Pyocyanin Increases Interleukin-8 Expression by Human Airway Epithelial Cells," *Infect. Immun.*, 1998, 66(12):5777-5784.

Douwes et al., "Biological agents—recognition," *Modern Industrial Hygiene*, vol. 2, 2003, J.L. Perkins (ed.), ACGIH, Cincinnati, pp. 219-292.

Frick et al., "*Haemophilus influenzae* Stimulates ICAM-1 Expression on Respiratory Epithelial Cells," *J. Immunol.*, 2000, 164:4185-4196.

Ganz, "Antimicrobial polypeptides in host defense of the respiratory tract," *J. Clin. Invest.*, 2002, 109:693-697.

García et al., "Human β-defensin 4: a novel inductible peptide with a specific salt-sensitive spectrum of antimicrobial activity," *FASEB J.*, 2001, 15:1819-1821.

Giardina et al., "Construction of Acetate Auxotrophs of *Neisseria meningitides* to Study Host-Meningococcal Endotoxin Interactions," *J. Biol. Chem.*, 2001, 276(8):5883-5891.

Gioannini et al., "Isolation of an endotoxin-MD-2 complex that produces Toll-like receptor 4-dependent cell activation at picomolar concentrations," *Proc. Natl. Acad. Sci. USA*, 2004, 101(12):4186-4191.

Gioannini et al., "An Essential Role for Albumin in the Interaction of Endotoxin with Lipopolysaccharide-binding Protein and sCD14 and Resultant Cell Activation," *J. Biol. Chem.*, 2002, 277(49):47818-47825.

Gioannini et al., "Regulation of interactions with endotoxin with host cells," *J. Endotoxin Res.*, 2003, 9(6):401-408.

Gottar et al., "The *Drosophila* immune response against Gram-negative bacteria is mediated by a peptidoglycan recognition protein," *Nature*, 2002, 416:640-644.

Hailman et al., "Lipopolysaccharide (LPS)-binding Protein Accelerates the Binding of LPS to CD14," *J. Exp. Med.*, 1994, 179:269-277.

Harder et al., "Mucoid *Pseudomonas aeruginosa*, TNF-α, and IL-1β, but Not IL-6, Induce Human β-Defensin-2 in Respiratory Epithelia," *Am. J. Respir. Cell Mol. Biol.*, 2000, 22:714-721.

Harder et al., "Isolation and Characterization of Human β-Defensin-3, a Novel Human Inducible Peptide Antibiotic," *J. Biol. Chem.*, 2001, 276(8):5707-5713.

Harder et al., "A peptide antibiotic from human skin," *Nature*, 1997, 387:861.

Higgins and Sharp, "Fast and sensitive multiple sequence alignments on a microcomputer," *CABIOS*, 1989, 5(2):151-153.

Higgins and Sharp, "CLUSTAL: a package for performing multiple sequence alignment on a microcomputer," *Gene*, 1988, 73:237-244.

Hoffman et al., "Phylogenetic Perspectives in Innate Immunity," *Science*, 1999, 284:1313-1318.

Huang et al., "Parallelization of a local similarity algorithm," *CABIOS*, 1992, 8(2):155-165.

Inzana et al., "Phase Variation and Conservation of Lipooligosaccharide Epitopes in *Haemophilus somnus*," *Infect. Immun.*, 1997, 65(11):4675-4681.

Iovine et al., "The Carboxyl-terminal Domain of Closely Related Endotoxin-binding Proteins Determines the Target of Protein-Lipopolysaccharide Complexes," *J. Biol. Chem.*, 2002, 277(10):7970-7978.

Janeway Jr. and Medzhitov, "Innate Immune Recognition," *Annu. Rev. Immunol.*, 2002, 20:197-216.

Jia et al., "Discovery of new human β-defensins using a genomics-based approach," *Gene*, 2001, 263:211-218.

Jia et al., "Endotoxin responsiveness of human airway epithelia is limited by low expression of MD-2," *Am. J. Physiol. Lung Cell Mol. Physiol.*, 2004, 287:L428-L437.

Jiang et al., "Cutting Edge: Lipopolysaccharide Induces Physical Proximity Between CD14 and Toll-Like Receptor 4 (TLR4) Prior to Nuclear Translocation of NF-κB[1]," *J. Immunol.*, 2000, 165:3541-3544.

Karlin and Altschul, "Methods for assessing the statistical significance of molecular sequence features by using general scoring schemes," *Proc. Natl. Acad. Sci. USA*, 1990, 87:2264-2268.

Karlin and Altschul, "Applications and statistics for multiple high-scoring segments in molecular sequences," *Proc. Natl. Acad. Sci. USA*, 1993, 90:5873-5877.

Karp et al., "An In Vitro Model of Differential Human Airway Epithelia," *Meth. Mol. Biol.*, 2002, 188:115-137.

Kawasaki et al., "Involvement of TLR4/MD-2 complex in species-specific lipopolysaccharide-mimetic signal transduction by Taxol," *J. Endotoxin Res.*, 2001, 7(3):232-236.

Kawasaki et al., "Identification of Mouse MD-2 Residues Important for Forming the Cell Surface TLR4-MD-2 Complex Recognized by Anti-TLR4-MD-2 Antibodies, and for Conferring LPS and Taxol Responsiveness on Mouse TLR4 by Alanine-Scanning Mutagenesis," *J. Immunol.*, 2003, 170:413-420.

Lamping et al., "LPS-binding Protein Protects Mice from Septic Shock Caused by LPS or Gram-negative Bacteria," *J. Clin. Invest.*, 1998, 101(10):2065-2071.

Latz et al., "Lipopolysaccharide Rapidly Traffics to and from the Golgi Apparatus with the Toll-like Receptor 4-MD-2-CD14 Complex in a Process That Is Distinct from the Initiation of Signal Transduction," *J. Biol. Chem.*, 2002, 277(49):47834-47843.

Lehninger, "The amino acid building blocks of proteins," *Biochemistry*, 1975, 2nd ed., pp. 73-75.

Lemaitre et al., "The Dorsoventral Regulatory gene Cassette *spätzle/Toll/Cactus* Controls the Potent Antifungal Response in Drosophila Adults," *Cell*, 1996, 86:973-983.

Lerman et al., "Nasopharyngeal Carriage of Antibiotic-Resistant *Haemophilus influenzae* in Healthy Children," *Pediatrics*, 1979, 64(3):287-291.

Liu et al., "Structure and mapping of the human β-defensin HBD-1 gene and its expression at sites of inflammation," *Gene*, 1998, 222:237-244.

Malley et al., "Recognition of pneumolysin by Toll-like receptor 4 confers resistance to pneumococcal infection," *Proc. Natl. Acad. Sci. USA*, 2003, 100(4):1966-1971.

Mathews et al., "Production of β-Defensin Antimicrobial Peptides by the Oral Mucosa and Salivary Glands," *Infect. Immun.*, 1999, 67(6):2740-2745.

McCray, Jr. and Bentley, "Human Airway Epithelia Express a β-defensin," *Am. J. Respir. Cell Mol. Biol.*, 1997, 16:343-349.

McCray, Jr. et al., "Alveolar Macrophages Inhibit Retrovirus-Mediated Gene Transfer to Airway Epithelia," *Hum. Gene Ther.*, 1997, 8:1087-1093.

McNamara et al., "Ocular Surface Epithelia Express mRNA for Human Beta Defesin-2," *Exp. Eye Res.*, 1999, 69:483-490.

Means et al., "The biology of Toll-like receptors," *Cytokine Growth Factor Rev.*, 2000, 11:219-232.

Medzhitov and Janeway, Jr., "An ancient system of host defense," *Curr. Opin. Immunol.*, 1998, 10:12-15.

Medzhitov and Janeway, Jr., "Innate immune recognition: mechanisms and pathways," *Immunol. Rev.*, 2000, 173:89-97.

Medzhitov et al., "A human homologue of the *Drosophila* Toll protein signals activation of adaptive immunity," *Nature*, 1997, 388:394-397.

Meinkoth and Wahl, "Hybridization of Nucleic Acids Immobilized on Solid Supports," *Anal. Biochem.*, 1984, 138:267-284.

Miyake, "Innate recognition of lipopolysaccharide by CD14 and toll-like receptor 4-MD-2: unique roles for MD-2," *Int. Immunopharmacol.*, 2003, 3:119-128.

Mueller-Annealing et al., "Ambient Endotoxin Concentrations in $PM_{10}$ from Southern California," *Environ. Health Pers.*, 2004, 112(5):583-588.

Mullen et al., "The role of disulfide bonds in the assembley and function of MD-2," *Proc. Natl. Acad. Sci. USA*, 2003, 100(7):3919-3924.

Munford et al., "Biosynthetic radiolabeling of bacterial lipopolysaccharide to high specific activity," *J. Immunol. Meth.*, 1992, 148:115-120.

Muroi et al., "MD-2, a Novel Accessory Molecule, Is Involved in Species-Specific Actions of *Salmonella* Lipid A," *Infect. Immun.*, 2002, 70(7):3546-3550.

Muroi et al., "Regions of the Mouse CD14 Molecule Required for Toll-like Receptor 2- and 4-mediated Activation of NF-κB," *J. Biol. Chem.*, 2002, 277(44):42372-42379.

Myers and Miller, "Optimal alignments in linear space," *CABIOS*, 1988, 4(1):11-17.

Nagai et al., "Essential role of MD-2 in LPS responsiveness and TLR4 distribution," *Nat. Immunol.*, 2002, 3(7):667-672.

Needleman and Wunsch, "A General Method Applicable to the Search for Similarities in the Amino Acid Sequence of Two Proteins," *J. Mol. Biol.*, 1970, 48:443-453.

Newman, "Therapeutic aerosols," *Aerosols and the Lung*, 1984, Clarke and Pavia (eds.), pp. 197-224, Butterworths, London, England.

Ohnishi et al., "N-Linked Glycosylations at Asn$^{26}$ and Asn$^{114}$ of Human MD-2 Are Required for Toll-Like Receptor 4-Mediated Activation of NF-κB by Lipopolysaccharide," *J. Immunol.*, 2001, 167:3354-3359.

O'Neil et al., "Expression and Regulation of the Human β-Defensins hBD-1 and hBD-2 in Intestinal Epithelium," *J. Immunol.*, 1999, 163:6718-6724.

Pearson and Lipman, "Improved tools for biological sequence comparison," *Proc. Natl. Acad. Sci. USA*, 1988, 85:2444-2448.

Pearson et al., "Using the FASTA Program to Search Protein and DNA Sequence Databases," *Meth. Mol. Biol.*, 1994, 24:307-331.

Re and Strominger, "Monomeric Recombinant MD-2 Binds Toll-like Receptor 4 Tightly and Confers Lipopolysaccharide Responsiveness," *J. Biol. Chem.*, 2002, 277(26):23427-23432.

Re and Strominger, "Separate Functional Domains of Human MD-2 Mediate Toll-Like Receptor 4-Binding and Lipopolysaccharide Responsiveness," *J. Immunol.*, 2003, 171:5272-5276.

Reynolds, "Integrated Host Defense Against Infections," *The Lung: Scientific Foundations*, 1997, Crystal et al. (eds.), Raven Press, Ltd., New York, NY, pp. 2353-2365.

Schröder and Harder, "Human beta-defensin-2," *Int. J. Biochem. Cell Biol.*, 1999, 31:645-651.

Schromm et al., "Molecular Genetic Analysis of an Endotoxin Nonresponder Mutant Cell Line: A Point Mutation in a Conserved Region of MD-2 Abolishes Endotoxin-induced Signalling," *J. Exp. Med.*, 2001, 194(1):79-88.

Schütt, "Molecules in focus: CD14," *Int. J. Biochem. Cell Biol.*, 1999, 31:545-549.

Schutte and McCray, Jr., "β-Defensins in Lung Host Defense," *Annu. Rev. Physiol.*, 2002, 64:709-748.

Schutte et al., "Discovery of five conserved β-defensin gene clusters using a computational search strategy," *Proc. Natl. Acad. Sci. USA*, 2002, 99(4):2129-2133.

Shimazu et al., "MD-2, a Molecule that Confers Lipopolysaccharide Responsiveness on Toll-like Receptor 4," *J. Exp. Med.*, 1999, 189(11):1777-1782.

Singh et al., "Production of γ-defensins by human airway epithelia," *Proc. Natl. Acad. Sci. USA*, 1998, 95:14961-14966.

Smith et al., "Endobronchial Infection in Cystic Fibrosis," *Acta Paediatr. Scand. Suppl.*, 1989, 363:31-36.

Smith and Waterman, "Comparison of Biosequences," *Adv. Appl. Math.*, 1981, 2:482-489.

Stryer, "Confirmation and Dynamics," *Biochemistry*, 2$^{nd}$ edition, W.H.Freeman and Co., San Francisco, 1981, pp. 14-15.

Takeda and Akira, "Toll receptors and pathogen resistance," *Cell. Microbiol.*, 2003, 5(3):143-153.

Tapping and Tobias, "Cellular Binding of Soluble CD14 Requires Lipopolysaccharide (LPS) and LPS-binding Protein," *J. Biol. Chem.*, 1997, 272(37):23157-23164.

Tauszig et al., "Toll-related receptors and the control of antimicrobial peptide expression in *Drosophila*," *Proc. Natl. Acad. Sci. USA*, 2000, 97(19):10520-10525.

Thomas et al., "Evidence of a trimolecular complex involving LPS, LPS binding protein and soluble C14 as an effector of LPS response," *FEBS Lett.*, 2002, 531:184-188.

Tsutsumi-Ishii and Nagaoka, "Modulation of Human β-Defensin-2 Transcription in Pulmonary Epithelial Cells by Lipopolysaccharide-Stimulated Mononuclear Phagocytes Via Proinflammatory Cytokine Production," *J. Immunol.*, 2003, 170:4226-4236.

Ulevitch and Tobias, "Recognition of Gram-negative bacteria and endotoxin by the innate immune system," *Curr. Opin. Immunol.*, 1999, 11:19-22.

Ulevitch, "Molecular Mechanisms of Innate Immunity," *Immunol. Res.*, 2000, 21(2):49-54.

Viriyakosol et al., "MD-2 Binds to Bacterial Lipopolysaccharide," *J. Biol. Chem.*, 2001, 276(41):38044-38051.

Visintin et al., "Lysines 128 and 132 Enable LPS Binding to MD-2, Leading to Toll-like Receptor 4 Aggregation and Signal Transduction," *J. Biol. Chem.*, 2003, 278(48):48313-48320.

Visintin et al., "Secreted MD-2 is a large polymeric protein that efficiently confers lipopolysaccharide sensitivity to Toll-like receptor 4," *Proc. Natl. Acad. Sci. USA*, 2001, 98(21):12156-12161.

Wang et al., "Increasing Epithelial Junction Permeability Enhances Gene Transfer to Airway Epithelia *In Vivo*," *Am. J. Respir. Cell Mol. Biol.*, 2000, 22:129-138.

Wang et al., "Toll-Like Receptor 4 Mediates Innate Immune Responses to *Haemophilus influenzae*, Infection in Mouse Lung," *J. Immunol.*, 2002, 168:810-815.

Yang et al., "Cellular Events Mediated by Lipopolysaccharide-stimulated Toll-like Receptor 4," *J. Biol. Chem.*, 2000, 275(27):20861-20866.

Yu and Wright, "Catalytic Properties of Lipopolysaccharide (LPS) Binding Protein," *J. Biol. Chem.*, 1996, 271:4100-4105.

Zasloff, "Antimicrobial peptides of multicellular organisms," *Nature*, 2002, 415:389-395.

Chow et al., "Toll-like Receptor-4 mediates lipopolysaccharide-induced signal transduction," *J. Biol. Chem.*, 1999, 274(16):10689-10692.

Hajjar et al., "Human Toll-like receptor 4 recognizes host-specific LPS modifications," 2002 Nature Immunology, 3(4):354-359.

Kennedy et al., "A complex of soluble MD-2 and lipopolysaccharide serves as an activating ligand for Toll-like receptor 4," *J. Biol. Chem.*, 2004, 279(33):34698-34704.

Takeuchi et al., "Differential roles of TLR2 and TLR4 in recognition of gram-negative and gram-positive bacterial cell wall components," 1999, Immunity 11:443-451.

International Search Report, PCT/US2004/038375.

* cited by examiner

|        | HAE | Mac |
|--------|-----|-----|
| TLR4   | band | band |
| CD14   | band | band |
| MD-2   |      | band |
| GAPDH  | band | band |
| RT     | −  + | −  + |

FIG. 7

ISOLATED COMPLEXES OF ENDOTOXIN AND MD-2

STATEMENT REGARDING FEDERALLY SPONSORED RESEARCH

Work related to this application was supported by grants from the National Institutes of Health (HL61234, HL59324, ES005605, AI24616, AI65298, and PO144642). The government may have certain rights in the invention.

BACKGROUND OF THE INVENTION

The ability of an organism to withstand bacterial invasion depends upon sensitive and specific molecular systems. The molecules involved in these systems are designed to recognize specific bacterial products and trigger rapid responses to small numbers of invading bacteria.

Innate recognition systems include highly conserved "pattern recognition" host molecules that detect and respond to highly conserved and structurally unique microbial molecules. The best-studied example of such an innate system is the machinery engaged in recognition of endotoxins, unique surface glycolipids of Gram-negative bacteria.

Potent pro-inflammatory cellular responses to endotoxin are mediated through activation of a member of the Toll-like receptor family of proteins, Toll-like receptor 4 (TLR4; Beutler et al., 2003; Means et al., 2000; and Ulevitch et al., 1999). An important feature of TLR4-dependent cell activation by endotoxin is its extraordinary sensitivity, permitting timely host responses to small numbers of invading Gram-negative bacteria, essential for efficient host defense (Beutler et al., 2003; Means et al., 2000; and Ulevitch et al., 1999).

TLR4 contains a leucine-rich extracellular domain involved in ligand recognition, a transmembrane region, and an intracellular domain responsible for triggering signalling pathways that result in activation of genes of the innate immune defense system (Beutler et al., 2001; and Medzhitov et al., 1998). Maximal potency of TLR4-dependent cell activation by endotoxin requires four different extracellular and cell surface host proteins: lipopolysaccharide (LPS) binding protein (LBP), CD14, MD-2 and TLR4 (Beutler et al., 2003; Miyake et al., 2003; and Ulevitch, 2000).

TLR4 requires MD-2 for CD14-dependent cellular response to low concentrations of endotoxin, but neither the precise nature of the ligand that binds to TLR4 or the role of MD-2 has been defined. MD-2, either endogenously expressed or exogenously added, associates with TLR4 on the cell surface (Viriyakosol et al., 2001; Schromm et al., 2001; Visintin et al., 2001; Re et al., 2002; Akashi et al., 2003; Visintin et al., 2003; and Re et al., 2003) and its endogenous expression is needed for optimal surface expression of TLR4. TLR4 responsiveness to endotoxin is disrupted by point mutations of MD-2 (Schromm et al., 2001; Kawasaki et al., 2003; Ohnishi et al., 2001; and Mullen et al., 2003) (e.g., C95Y, Lys128 and 132) despite surface expression of TLR4/MD-2 complexes.

SUMMARY OF THE INVENTION

The activation of inflammatory reactions mobilizes protective host defenses. However, excessive responses, or dysfunctional regulation of these responses, can lead to severe, even life-threatening pathology. Thus, optimal physiological functioning of inflammatory responses requires careful positive and negative regulation. Accordingly, agents and methods that affect such regulation, for example, by affecting TLR4-mediated cell activation, would have great clinical benefit and are needed.

Applicants have discovered that complexes containing endotoxin species with potent pro-inflammatory activity induce TLR4-dependent cell activation at pM concentrations. Complexes containing under-acylated forms of endotoxin have little or no agonist activity and antagonize pro-inflammatory activity of TLR4 agonists. In contrast to endotoxin alone, these complexes are water soluble and, in contrast to MD-2 alone, they are uniformly monomeric. Complexes with potent TLR4 agonist activity may be used to prime innate and adaptive host immune responses whereas complexes that function as potent TLR4 antagonists may be used to dampen uncontrolled endotoxin-driven inflammation.

Applicants have produced and isolated complexes of endotoxin and MD-2. Applicants have discovered that endotoxin-MD-2 complexes containing wild-type endotoxin produce TLR4-dependent cell stimulation, while complexes containing mutant forms of endotoxin, for example, under-acylated forms of endotoxin, inhibit TLR4-dependent cell stimulation. Applicants have also discovered that MD-2 can have inhibitory as well as stimulatory effects on TLR4-dependent cell activation by endotoxin.

Accordingly, the present invention provides a purified complex including endotoxin bound to MD-2. Surprisingly, these complexes, devoid of any other host or microbial molecules, are potent and water soluble, not requiring additional lipid carrier molecules (e.g., serum albumin) for water solubility. The present invention also provides a method for making the complexes of the invention and a method of isolating complexes of the invention.

The present invention also provides methods of using the complexes of the invention, e.g., methods to increase or inhibit TLR4-dependent activation of cells by endotoxin in vitro or in vivo. Methods using complexes with mutant endotoxin are useful, e.g., to decrease undesirable endotoxin-mediated inflammation. Methods using complexes with wild-type endotoxin are useful, e.g., to promote innate immune responses and as immunological adjuvants.

BRIEF DESCRIPTION OF THE FIGURES

FIGS. 1A and 1B depict SDS-PAGE immunoblots. FIG. 1C depicts extracellular IL-8 as assayed by ELISA. FIG. 1D depicts cell activation.

FIGS. 2A and 2B depict analysis of [$^{14}$C]-LOS. FIG. 2C depicts cell activation. FIGS. 2D and 2E depict adsorption and elution of bioactive M$_r$~25,000 complex.

FIG. 4A depicts extracellular accumulation of IL-8. FIG. 4B depicts analysis of [$^{14}$C]-LOS by liquid scintillation spectroscopy. FIG. 4C depicts amounts of radioactivity associated with cells.

FIGS. 6A and 6B depict changes in HBD-2 MRNA expression.

FIG. 7 depicts expression of components of innate immune signaling in human airway epithelia.

FIG. 9A depicts results indicating that MD-2 complementation of well-differentiated polarized human airway epithelia confers enhanced responsiveness to LOS. FIG. 9B depicts results indicating that MD-2 complementation confers enhanced responsiveness to endotoxin. FIG. 9C depicts results indicating that MD-2 complementation of airway epithelia confers enhanced responsiveness to LOS-sCD14 complexes. FIG. 9D depicts results indicating that complementation of airway epithelia with recombinant MD-2 protein (rMD-2) confers enhanced responsiveness to endotoxin.

DETAILED DESCRIPTION OF THE INVENTION

Figure 1:
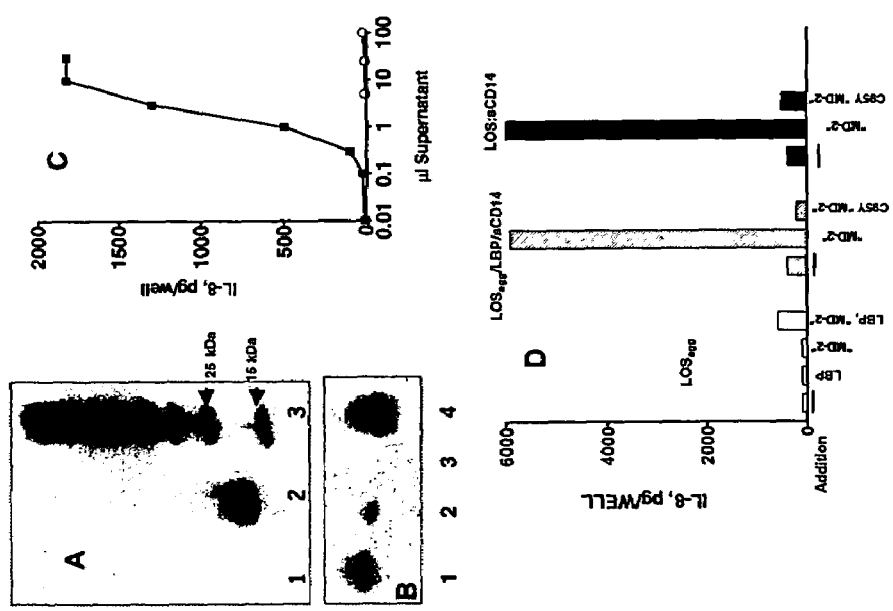
FIG. 1 depicts the expression and bioactivity of recombinant MD-2-His$_6$.

Applicants have discovered that MD-2 interacts directly with endotoxin-CD14 complexes to generate endotoxin-MD-2 complexes that produce TLR4-dependent cell stimulation. This stimulation can be produced at concentrations consistent with the ability of the innate immune system to detect and respond to minute amounts of endotoxin. Thus, endotoxin bound to MD-2, rather than endotoxin itself, is a ligand for triggering TLR4 receptor activation.

Accordingly, the present invention provides a purified complex including endotoxin bound to MD-2. The endotoxin may be a wild-type endotoxin. The endotoxin may be a wild-type endotoxin derived from any of a broad array of Gram-negative bacterial species. This includes many species of clinical importance such as *Neisseria meningitidis, Escherichia coli, Pseudomonas aeruginosa, Haemophilus influenzae, Salmonella typhimurium*, and *Francisella tularensis*.

The complex may have a molecular weight of about 25,000. The complex may consist essentially of one molecule of endotoxin bound to one molecule of MD-2. The complex may be soluble in water. The complexes may be soluble in water to a greater extent than is an endotoxin molecule not bound to MD-2. The complex may bind to TLR4 and may produce TLR4-dependent activation of cells, e.g., at a concentration of about 1 nM or less of the complex the complex may produce a half maximal activation of cells, e.g., at a concentration of about 30 pM or less of the complex the complex may produce a half maximal activation of cells.

The endotoxin may be hexa-acylated. The endotoxin may be an under-acylated endotoxin, e.g., a tetra-acylated or penta-acylated endotoxin. Examples of such under-acylated endotoxins are in PCT Publication No. WO 97/19688. The complex containing the under-acylated endotoxin may be capable of producing less TLR4-dependent activation of cells as compared to a complex including an endotoxin that is hexa-acylated. The complex containing the under-acylated endotoxin also may inhibit cell activation by more potent TLR4 agonists.

The present invention also provides a composition including a complex of the invention, optionally including a pharmaceutically acceptable carrier. The composition can be used, e.g., to promote innate immune responses and as an immunological adjuvants.

The present invention also provides methods to produce the complexes of the invention. This method includes contacting MD-2 with an endotoxin-CD14 complex to produce the endotoxin-MD-2 complex. The endotoxin can be modified by LBP prior to the formation of the endotoxin-MD-2 complex.

The present invention also provides a method for modulating TLR4-mediated cell activation by endotoxin, including administering to the cell MD-2. The MD-2 can be administered prior to exposure of the cell to endotoxin. The MD-2 can be administered while the cell is exposed to endotoxin. In some embodiments of the invention, administration of a stoichiometric excess of MD-2 relative to TLR4 inhibits the endotoxin-mediated cell activation. In some embodiments of the invention, the MD-2 is administered to achieve a concentration of about 10–100 ng/ml. In some embodiments of the invention, administration of MD-2 to cells, e.g. cells having a constitutively low level of MD-2 expression, increases endotoxin-mediated cell activation. These cells may be, for example, airway epithelial cells or pulmonary macrophages.

The present invention also provides methods for treating conditions associated with endotoxin-mediated cell activation. The conditions include sepsis, trauma, liver disease, inflammatory bowel disease, cystic fibrosis, asthma, complications in renal dialysis, autoimmune diseases, cancer chemotherapy sequelae, and intracellular gram-negative bacterial infections, e.g., infection caused by *Francisella tularensis*. The conditions can be treated by administration of a complex of the invention. Treatment, as used herein, includes both prophylactic treatments and therapeutic treatments.

Endotoxin and MD-2

The complexes of the invention are formed by the association of endotoxin with MD-2. The endotoxin molecules and the MD-2 molecules may be wild-type molecules, or they may be mutant molecules. In some embodiments of the invention, the endotoxin molecules are wild-type endotoxin molecules, e.g., endotoxin derived from wt gram-negative bacteria. These wild-type endotoxin molecules may be hexa-acylated. The complexes formed with the wild-type endotoxin and MD-2 are capable of binding to TLR4 and are capable of producing TLR4-dependent cell activation.

In some embodiments of the invention, the endotoxin molecules are mutant endotoxin molecules. In some embodiments of the invention, the mutant endotoxin molecules are endotoxin molecules that are capable of binding to MD-2 and these complexes to TLR4 without producing the same level of TLR4-dependent cell activation (ie., the mutant endotoxin complexes produce less activation) as produced by TLR4 dependent cell activation by complexes containing containing wild-type endotoxin molecules. These mutant endotoxin molecules may be under-acylated (e.g., penta-acylated or tetra-acylated). These under-acylated endotoxin molecules may be produced via enzymatic release of non-hydroxylated fatty acids from endotoxin, or they may be produced using bacteria having genes disrupted that encode an acyltransferase (e.g., htrB, msbB) needed for biosynthetic incorporation of non-hydroxylated fatty acids into endotoxin. Because the complexes are both potent and water soluble, they will be useful in the treatment of conditions associated with TLR4-dependent cell activation.

The MD-2 molecule may also be a wild-type MD-2 or a mutant MD-2 molecule. The MD-2 may be a recombinant MD-2.

TLR4-dependent cell activation refers to the cascade of events produced when TLR4 is activated, e.g. by endotoxin, to produce responses, e.g., pro-inflammatory responses. TLR4-dependent cell activation can be measured by the art worker, e.g., by assaying the level of IL-8 produced by the cells.

As used herein, the endotoxin and MD-2 proteins include variants or biologically active fragments of the proteins. A "variant" of the protein is a protein that is not completely identical to a native protein. A variant protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall polypeptide retains its spacial conformation but has altered biological activity. For example, common conserved changes might be Asp to Glu, Asn or Gln; His to Lys or Arg or Phe; Asn to Gln, Asp or Glu and Ser to Cys, Thr or Gly. Alanine is commonly used to substitute for other amino acids in mutagenesis studies. The 20 essential amino acids can be grouped as follows: alanine, valine, leucine, isoleucine, proline, phenylalanine, tryptophan and methionine having nonpolar side chains; glycine, serine, threonine, cysteine, tyrosine, asparagine and glutamine having uncharged polar side chains; aspartate and glutamate having acidic side chains; and lysine, arginine, and histidine having basic side chains (Stryer, L. *Biochemistry* (2d edition) W. H. Freeman and Co. San Francisco (1981), p. 14–15; Lehninger, A. *Biochemistry* (2d ed., 1975), p. 73–75).

It is known that variant polypeptides can be obtained based on substituting certain amino acids for other amino acids in the polypeptide structure in order to modify or improve biological activity. For example, through substitution of alternative amino acids, small conformational changes may be conferred upon a polypeptide that result in increased bioactivity.

One can use the hydropathic index of amino acids in conferring interactive biological function on a polypeptide, wherein it is found that certain amino acids may be substituted for other amino acids having similar hydropathic indices and still retain a similar biological activity.

The amino acid sequence of the variant endotoxin or MD-2 protein corresponds essentially to the native protein amino acid sequence. As used herein "corresponds essentially to" refers to a polypeptide sequence that will elicit a biological response substantially the same as the response generated by native protein. Such a response may be at least 60% of the level generated by native protein, and may even be at least 80%, 85%, 90% or 95% of the level generated by native protein. For example, variants of the native endotoxin will elicit a biological response (i.e., TLR4-dependent cell activation) substantially the same as the response generated by the native endotoxin.

A variant of the invention may include amino acid residues not present in the corresponding native protein, or may include deletions relative to the corresponding native protein. A variant may also be a truncated fragment as compared to the corresponding native protein, i.e., only a portion of a full-length protein. Protein variants also include peptides having at least one D-amino acid.

The endotoxin and/or MD-2 of the present invention may be expressed from isolated nucleic acid (DNA or RNA) sequences encoding the proteins. Amino acid changes from the native to the variant protein may be achieved by changing the codons of the corresponding nucleic acid sequence. Recombinant is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence.

The starting material (such as an MD-2 gene) used to make the complexes of the present invention may be substantially identical to wild-type genes, or may be variants of the wild-type gene. Further, the polypeptide encoded by the starting material may be substantially identical to that encoded by the wild-type gene, or may be a variant of the wild-type gene. The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may include additions or deletions (i.e., gaps) compared to the reference sequence (which does not include additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, *CABIOS*, 4:11 (1988); the local homology algorithm of Smith et al., *Adv. Appl. Math.*, 2:482 (1981); the homology alignment algorithm of Needleman and Wunsch, *JMB*, 48:443 (1970); the search-for-similarity-method of Pearson and Lipman, *Proc. Natl. Acad. Sci. USA*, 85:2444 (1988); the algorithm of Karlin and Altschul, *Proc.*

*Natl. Acad. Sci. USA*, 87:2264 (1990), modified as in Karlin and Altschul, *Proc. Natl. Acad. Sci. USA*, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene*, 73:237 (1988); Higgins et al., *CABIOS*, 5:151 (1989); Corpet et al., *Nucl. Acids Res.*, 16:10881 (1988); Huang et al., *CABIOS*, 8:155 (1992); and Pearson et al., *Meth. Mol. Biol.*, 24:307 (1994). The ALIGN program is based on the algorithm of Myers and Miller, supra. The BLAST programs of Altschul et al., *JMB*, 215: 403 (1990); *Nucl. Acids Res.*, 25:3389 (1990), are based on the algorithm of Karlin and Altschul supra.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., *Nucleic Acids Res*. 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See http://www.ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide includes a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide includes a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. Bind(s) substantially refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA—DNA hybrids, the $T_m$ can be approximated from the equation of Meinkoth and Wahl, *Anal. Biochem.*, 138:267 (1984); $T_m$ 81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acid Probes*, part I chapter 2 "Overview of principles of hybridization and the strategy of nucleic acid probe assays" Elsevier, N.Y. (1993). Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Molecular Cloning: A Laboratory Manual (Sambrook et al., 3rd Ed., Cold Spring Harbor Laboratory Press, (2001) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Complexes of Endotoxin with MD-2

Disclosed herein is the formation and isolation of a novel, bioactive, monomeric endotoxin-MD-2 complex. The complex can be generated with about physiologic (pM) concentrations of endotoxin and soluble MD-2. This complex, at pg/ml concentrations, activates cells in a TLR4-dependent fashion without the inclusion of other host or bacterial factors. The surprising and unexpected success in achieving formation of a bioactive endotoxin-MD-2 complex at such low concentrations of endotoxin and MD-2 reflects the importance of presenting endotoxin to MD-2 after endotoxin has been first modified by LBP and CD14. As interactions of CD14 with endotoxin are greatly enhanced by prior interaction of endotoxin with LBP (Gioannini et al., 2002; Iovine et al., 2002; Hailman et al., 1994; Yu et al., 1996; Tapping et al., 1997; Thomas et al., 2002; and Giardina et al., 2001), these findings indicate that MD-2-endotoxin interactions leading to the generation of the bioactive endotoxin-MD-2 complex are greatly enhanced by presentation of endotoxin as a monomeric complex with CD14. This may reflect, for example, a greater reactivity of MD-2 for disaggregated vs. aggregated forms of endotoxin, or the need for an additional protein-protein interaction between CD14 and MD-2. Whatever the precise molecular basis of the high affinity and reactivity of endotoxin-CD14 complexes with MD-2, these surprising findings indicate a direct role of MD-2 in endotoxin recognition and delivery of endotoxin to host cells containing TLR4 (FIGS. 2C and 3), not requiring prior association of MD-2 with TLR4, as has been previously presumed (Viriyakosol et al., 2001; Visinin et al., 2001; Visintin et al., 2003; and Mullen et al., 2003). These findings also indicate that the key role of LBP and CD14 in enhancing cell responses to endotoxin is to transform aggregates of endotoxin to monomeric endotoxin-CD14 complexes that are preferentially reactive with MD-2 (Table 1). Conversely, the remarkably potent activity of the purified endotoxin-MD-2 complex toward HEK/TLR4 cells indicates that CD14 is not needed as part of a more complex hetero-oligomeric receptor, as previously suggested (Miyake, 2003; Kawasaki et al., 2003; Muroi et al., 2002; Latz et al., 2002; and da Silva Correia et al., 2001).

The reaction pathway described herein in which endotoxin molecules in purified aggregates (or membranes) containing thousands to millions of endotoxin molecules/particle are extracted and transferred to first CD14 and then MD-2 provides a unique physico-chemical mechanism to attain the potency that is needed for response. The ability to generate a homogeneous protein-endotoxin complex that, alone, triggers TLR4-dependent cell activation, interacts with host cells in an almost exclusively TLR4-dependent fashion (FIG. 3) and that can be metabolically labelled to sufficient specific radioactivity to monitor interactions at pM concentrations makes it possible for the first time to measure host cell-endotoxin interactions that are directly relevant to TLR4-dependent cell activation.

Many endotoxin-responsive cells contain membrane-associated CD14 and MD-2 (associated with TLR4) (Means et al., 2000; Miyake et al., 2003; Takeda et al., 2003). However, as described herein, resting airway epithelial cells, like HEK/TLR4 cells, express TLR4 without MD-2 and respond to endotoxin only if LBP, sCD14 and soluble MD-2 are added. Each of these proteins are likely to be present in biological fluids at the concentrations needed to drive endotoxin-dependent TLR4 activation, especially in view of the very low extracellular MD-2 concentrations demonstrated in this study to be sufficient (FIG. 1D). Thus, the reaction pathway defined is relevant at the cell surface when TLR4/MD-2 complexes are endogenously present and also when only TLR4 is present at the cell surface and MD-2, which has been produced and secreted by neighboring cells, is present in the extracellular medium.

The findings presented herein thus indicate that MD-2 can engage both endotoxin and TLR4 and that simultaneous interaction of MD-2 with endotoxin and TLR4 is important for TLR4-dependent cell activation by endotoxin. It is thus predicted that binding sites within MD-2 for TLR4 and endotoxin are topologically as well as structurally distinct, permitting engagement of endotoxin-MD-2 complexes with TLR4, as the findings presented herein indicate (FIG. 3), as well as interaction and transfer of endotoxin from endotoxin-CD14 complexes to MD-2 already associated with TLR4 (FIG. 5). The complete lack of reactivity of the C95Y MD-2 mutant with endotoxin-sCD14 (FIG. 1D) explains the complete absence of activity in this mutant protein (FIG. 2B) despite a partial retention of reactivity with TLR4 (FIG. 4A).

In contrast to [$^{14}$C]-LOS-sCD14, the "stability/solubility" of LOS-MD-2 in aqueous buffer and its bioactivity does not require albumin (data not shown). That albumin is no longer required once the endotoxin-MD-2 complex is formed indicates that a hydrophobic site in MD-2, possibly a deep hydrophobic site, accommodates and shields the hydrophobic lipid A region of the bound endotoxin making subsequent transfer to TLR4 less likely. Thus, binding of endotoxin to MD-2 may induce conformational changes in MD-2 that lead to TLR4 activation (FIG. 5).

FIG. 5 depicts mechanisms of action of MD-2 in endotoxin-dependent activation of TLR4. TLR4 activation may involve (A) conformational changes in MD-2 that follow the interaction of MD-2 with endotoxin and TLR4 and/or (B) transfer of endotoxin from MD-2 to TLR4.

MD-2 may be able to discriminate between TLR4 agonists and antagonists. Agonists and antagonists may differ in their ability to form a complex with MD-2 or in the structural properties of the endotoxin-MD-2 complex that is formed. Perhaps, only endotoxins that are TLR4 agonists are transferred from CD14 to MD-2 or, within the endotoxin-MD-2 complex, trigger changes in MD-2 conformation or protein-protein contacts between TLR4 and MD-2 needed for TLR4 activation. Therefore, rather than transferring the buried endotoxin molecule to TLR4, MD-2 may function in a manner analogous to that observed with Toll receptors in *Drosophila* where a modified protein, Spaetzle, is the ligand that initiates the cytoplasmic signaling pathway.

Endotoxin Responsiveness of Human Airway Epithelia

The surfaces of the conducting airways and alveoli of the lung are a large interface between the host and the environment. Despite ongoing daily exposure to microbes and their components by inhalation, the intrapulmonary airways and airspaces normally maintain a sterile state without significant inflammation (Reynolds, 1997). This remarkable condition reflects the success of the concerted activities of the innate and adaptive immune systems.

Inducible antimicrobial peptides, including the cationic β-defensins, represent an important component of the innate immune system (Zasloff, 2002; Schutte et al., 2002; and Ganz, 2002). In humans, the expression of four β-defensins has been reported in pulmonary epithelia (McCray et al., 1997; Schroder et al., 1999; Bals et al., 1998; Jia et al., 2001; Harder et al., 2001; and Garcia et al., 2001), and a recent genome-wide search uncovered evidence of a much larger family of β-defensin genes encoded in five chromosomal clusters (Schutte et al., 2002).

Human β-defensin-2 (HBD-2) is an inducible cationic antimicrobial peptide expressed at many muscosal surfaces including the skin, cornea, gut, gingiva and airway epithelium (Bals et al., 1998; Harder et al., 1997; Mathews et al., 1999; O'Neil et al., 1999; Liu et al., 1998; and McNamara et al., 1999). In the airways, HBD-2 MRNA is expressed at low levels in resting cells but is markedly induced by pro-inflammatory stimuli including IL-1β, TNF-α, and *Pseudomonas aeruginosa* (Singh et al., 1998; and Harder et al., 2000). Furthermore, the 5' flanking sequence of the HBD-2 gene contains several cis-acting elements that may mediate transcription in response to inflammatory stimuli, including NF-κB, IFN-gamma, AP-1, and NF-IL-6 response elements (Liu et al., 1998; Harder et al., 2000; and Tsutsumi-Ishii et al., 2003).

The expression of inducible antimicrobial peptides such as human β-defensin-2 (HBD-2) by epithelia is a component of the innate pulmonary defense. It is herein reported that primary cultures of well-differentiated human airway epithelia express the mRNA for TLR4 but little or no MD-2 mRNA and display little HBD-2 expression in response to treatment with purified endotoxin+/–LBP and sCD14. Expression of endogenous MD-2 by transduction of airway epithelial cells with an adenoviral vector encoding MD-2 or extracellular addition of recombinant MD-2 both increased the responses of airway epithelia to endotoxin+LBP and sCD14 by >100-fold, as measured by NF-κB-luciferase activity and HBD-2 mRNA expression. MD-2 mRNA was induced in airway epithelia by exposure of these cells to specific bacterial or host products (e.g. killed *H. influenzae*, the P6 outer membrane protein from *H. influenzae*, or TNF-α+INF-γ). These findings indicate that MD-2, either co-expressed with TLR4 or secreted when produced in excess of TLR4 from neighboring cells, is required for airway epithelia to respond sensitively to endotoxin. The regulation of MD-2 expression in airway epithelia and pulmonary macrophages thus serves as a means to enhance or dampen endotoxin responsiveness in the airway.

Hypo-responsiveness to endotoxin is a common characteristic of epithelial cells lining mucosal surfaces that are repeatedly exposed to Gram-negative bacteria or cell-free (sterile) forms of endotoxin. The molecular basis of endotoxin hypo-responsiveness is unknown. As sensitive responses to endotoxin generally depend on TLR4-dependent signaling (Shimazu et al., 1999), hypo-responsiveness likely represents the functional deficiency of one or more elements of pathway(s) leading to and resulting from TLR4 activation. TLR4 is a membrane protein containing repeats of a leucine rich motif in the extracellular portion of the protein and a cytoplasmic domain homologous to the intracellular domain of the human IL-1 receptor (Medzhitov et al., 1997). The IL-1 responsiveness of airway epithelia indicates that the overlapping intracellular signaling pathways for activated TLR and IL-1 receptors (Hoffmann et al., 1999; Janeway et al., 2002; and Beutler et al., 2003) are present and functionally intact in human airway epithelia, including those important in NF-κ-B-regulated HBD-2 expression. Even though airway epithelia express TLR4, the cells responded poorly to LOS-sCD14. Therefore it is likely that there is a defect in TLR4-dependent recognition and/or response to endotoxin.

MD-2, also termed lymphocyte antigen 96 (LY96), was first identified by Shimazu and colleagues as a molecule that conferred TLR4-dependent responses to minute amounts of endotoxin (Shimazu et al., 1999; and Yang et al., 2000). Cells that are TLR4$^+$/MD-2$^-$ are virtually unresponsive to endotoxin (Shimazu et al., 1999; and Nagai et al., 2002). As described herein, human airway epithelia exhibit endotoxin responses consistent with a TLR4$^+$/MD-2$^-$ phenotype. The complementation of this deficiency of MD-2 via endogenous expression or extracellular addition was sufficient to convert human airway epithelia from endotoxin hypo-responsive to highly endotoxin responsive without changing basal NF-κB-regulated HBD-2 expression of these cells or that stimulated by treatment with an unrelated agonist (e.g., IL-1β). These data indicate that the hypo-responsiveness of "resting" airway epithelia is due specifically to the absence of MD-2 expression.

Results presented herein indicate that MD-2 plays a direct role in endotoxin recognition by TLR4. Endotoxin is transferred from an endotoxin-(s)CD14 complex to MD-2 to form an endotoxin-MD-2 complex that appears to be the ligand for endotoxin-dependent TLR4 activation. TLR4 alone has no apparent ability to productively engage the endotoxin-(s)CD14 complex. In addition, endogenous expression of MD-2 can increase surface expression of TLR4, as a TLR4/MD-2 complex, indicating a chaperone-like function for MD-2 as well. The ability of exogenously added MD-2 to increase cellular responsiveness to LOS-sCD14 and the ability of purified LOS-MD-2 to directly activate "resting" airway epithelia indicates some apical surface expression of TLR4 even without endogenous expression of MD-2. This would be biologically important because it would permit TLR4 from one cell to engage MD-2 or endotoxin-MD-2 derived from MD-2 secreted by a neighboring cell.

Figure 10:
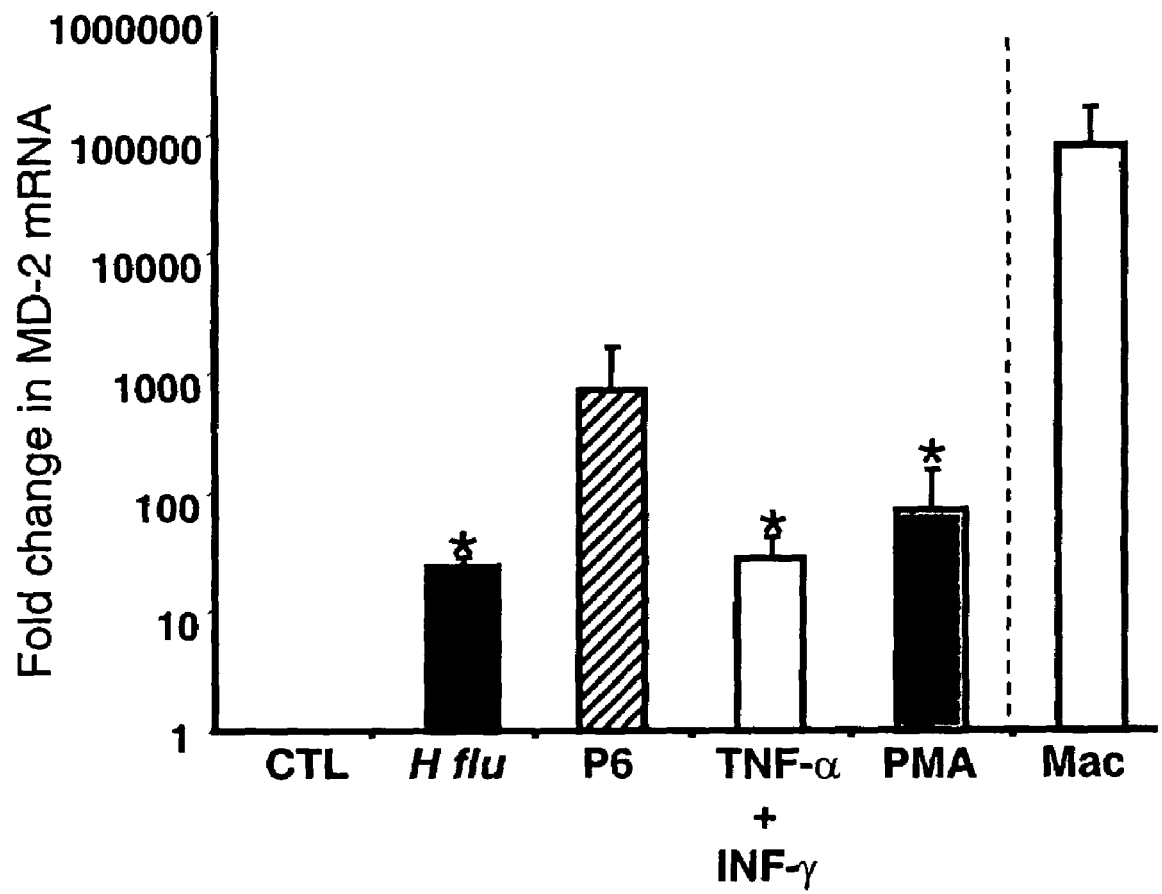
FIG. 10 depicts results indicating that MD-2 mRNA expression in human airway epithelia is inducible in response to several stimuli.

Thus, these results indicate that the regulation of MD-2 expression is a key determinant of airway epithelial responses to endotoxin. Under resting conditions, low MD-2 expression in airway epithelia renders cells poorly responsive to endotoxin, whereas up-regulation of MD-2 alone can greatly enhance cellular responses to endotoxin. As shown in FIG. 10, a variety of stimuli can induce MD-2 mRNA expression in airway epithelia, perhaps by more than one receptor-mediated pathway. MD-2 can be secreted by epithelia or mononuclear cells and the application of secreted MD-2 enhances TLR4 signaling in MD-2 deficient cells. There may be stimuli (e.g., cytokines, bacterial products) that induce MD-2 expression in airway epithelia to levels sufficient to enhance endotoxin responsiveness. In intestinal epithelia, expression of MD-2 is regulated by cytokine signals including TNF-α and interferon-γ (Abreu et al., 2001; and Visintin et al., 2001). Stimulated pulmonary macrophages might also secrete sufficient MD-2 to enhance TLR4 signaling in epithelia. In either case, production of MD-2 by epithelia or exogenous provision of MD-2 from neighboring cells would complement the airway cells for enhanced TLR4 signaling in response to endotoxin.

One advantage of such a hierarchy of responses is that it would help to minimize the frequency of epithelial-induced inflammatory signals from endotoxin. Ambient air contains bacteria and endotoxin (Mueller-Anneling et al., 2003) and the aerosolized concentrations of endotoxin can increase dramatically in some agricultural and industrial environments from $\leq 10$ EU/m$^3$ to >1,000 EU/m$^3$ (Douwes et al., 2003). Under normal conditions, the low expression of MD-2 in epithelia can serve to dampen endotoxin responsiveness to common environmental exposures and thereby avoid unwanted states of chronic inflammation in the face of frequent encounters with environmental endotoxin and other bacterial cell wall components. Conversely, up-regulation of MD-2 expression can be important to enhance host defense responses to invading Gram-negative bacteria. However, in certain disease states, such as cystic fibrosis or asthma, enhanced expression of MD-2 could lead to exaggerated endotoxin responsiveness with pathologic consequences.

Formulations and Administration

Complexes containing wild-type endotoxin produce TLR4-dependent cell stimulation, while complexes containing mutant forms of endotoxin inhibit TLR4-dependent cell stimulation. Methods of using the complexes, e.g., methods to increase or inhibit TLR4-dependent activation of cells by endotoxin in vitro or in vivo are provided. Methods using complexes with mutant endotoxin are useful, e.g., to decrease undesirable endotoxin-mediated inflammation. Methods using complexes with wild-type endotoxin are useful, e.g., to promote innate immune responses and to serve as an immunological adjuvant.

Complexes of the invention, or MD-2 alone, including their salts, can be administered to a patient. Administration in accordance with the present invention may be in a single dose, in multiple doses, and/or in a continuous or intermittent manner, depending, for example, upon the recipient's physiological condition, whether the purpose of the administration is therapeutic or prophylactic, and other factors known to skilled practitioners. The administration may be essentially continuous over a preselected period of time or may be in a series of spaced doses. The amount administered will vary depending on various factors including, but not limited to, the condition to be treated and the weight, physical condition, health, and age of the patient. Such factors can be determined by a clinician employing animal models or other test systems that are available in the art.

To prepare the complexes, the complexes are produced as described herein or otherwise obtained and purified as necessary or desired.

One or more suitable unit dosage forms including the complex can be administered by a variety of routes including topical, oral, parenteral (including subcutaneous, intravenous, intramuscular and intraperitoneal), rectal, dermal, transdermal, intrathoracic, intrapulmonary and intranasal (respiratory) routes.

The formulations may, where appropriate, be conveniently presented in discrete unit dosage forms and may be prepared by any of the methods known to the pharmaceutical arts. Such methods include the step of mixing the complex with liquid carriers, solid matrices, semi-solid carriers, finely divided solid carriers or combinations thereof, and then, if necessary, introducing or shaping the product into the desired delivery system. By "pharmaceutically acceptable" it is meant a carrier, diluent, excipient, and/or salt that is compatible with the other ingredients of the formulation, and not deleterious or unsuitably harmful to the recipient thereof. The therapeutic compounds may also be formulated for sustained release, for example, using microencapsulation (see WO 94/07529, and U.S. Pat. No. 4,962,091).

The complex may be formulated for parenteral administration (e.g., by injection, for example, bolus injection or continuous infusion) and may be presented in unit dose form in ampoules, pre-filled syringes, small volume infusion containers or in multi-dose containers. Preservatives can be added to help maintain the shelve life of the dosage form. The complex and other ingredients may form suspensions, solutions, or emulsions in oily or aqueous vehicles, and may contain formulatory agents such as suspending, stabilizing and/or dispersing agents. Alternatively, the complex and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers and vehicles that are available in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$–$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add other ingredients such as antioxidants, surfactants, preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions at a pH of about 7.0–8.0.

The complex can also be administered via the respiratory tract. Thus, the present invention also provides aerosol pharmaceutical formulations and dosage forms for use in the methods of the invention. In general, such dosage forms include an amount of complex effective to treat or prevent the clinical symptoms of a specific condition. Any attenuation, for example a statistically significant attenuation, of one or more symptoms of a condition that has been treated pursuant to the methods of the present invention is considered to be a treatment of such condition and is within the scope of the invention.

For administration by inhalation, the composition may take the form of a dry powder, for example, a powder mix of the complex and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197–224, Butterworths, London, England, 1984).

The complex may also be administered in an aqueous solution, for example, when administered in an aerosol or inhaled form. Thus, other aerosol pharmaceutical formulations may include, for example, a physiologically acceptable buffered saline solution. Dry aerosol in the form of finely divided solid compound that is not dissolved or suspended in a liquid is also useful in the practice of the present invention.

For administration to the respiratory tract, for example, the upper (nasal) or lower respiratory tract, by inhalation, the complex can be conveniently delivered from a nebulizer or a pressurized pack or other convenient means of delivering an aerosol spray. Pressurized packs may include a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker). The complex may also be delivered via an ultrasonic delivery system. In some embodiments of the invention, the complex may be delivered via an endotracheal tube. In some embodiments of the invention, the complex may be delivered via a face mask.

Furthermore, the complex may also be used in combination with other therapeutic agents, for example, pain relievers, anti-inflammatory agents, antihistamines, and the like, whether for the conditions described or some other condition.

The present invention further pertains to a packaged pharmaceutical composition such as a kit or other container. The kit or container holds a therapeutically effective amount of a pharmaceutical composition of the complex and instructions for using the pharmaceutical composition for treating a condition.

The invention will now be illustrated by the following non-limiting Examples.

EXAMPLE 1

Isolation of an Endotoxin-MD-2 Complex

Reported herein is the purification of a stable, monomeric, bioactive endotoxin-MD-2 complex generated by treatment of endotoxin-sCD14 with recombinant MD-2. Efficient generation of this complex occurred with pM amounts of endotoxin and ng/ml amounts of MD-2 and, under these conditions, required the presentation of endotoxin to MD-2 as a monomeric endotoxin-CD14 complex. Higher concentrations of the monomeric endotoxin-MD-2 complex can be generated by co-incubation of higher concentrations of soluble MD-2 and monomeric endotoxin-CD14 complex. TLR4-dependent delivery of endotoxin to human embryonic kidney (HEK) cells and cell activation at pM concentrations of endotoxin occurred with purified endotoxin-MD-2 complex, but not purified endotoxin aggregates±LBP and/or sCD14. The presence of excess MD-2 inhibited delivery of endotoxin-MD-2 to HEK/TLR4 cells and cell activation. These findings demonstrate that TLR4-dependent activation of host cells by pM concentrations of endotoxin occurs by sequential interaction and transfer of endotoxin to LBP, CD14 and MD-2 and simultaneous engagement of endotoxin and TLR4 by MD-2.

Recombinant MD-2 Secreted by Infected Insect Cells

Conditioned insect cell culture medium containing soluble, polyhistidine-tagged recombinant wild-type (wt) or C95Y mutant MD-2 were generated according to the method of Viriyakosol et al. (2001). A human embryonic kidney cell line (HEK293) that stably expresses TLR4 (HEK/TLR4), but lacks both CD14 and MD-2 (Yang et al., 2000), was used to evaluate the effect of MD-2 on the ability of lipooligosaccharide (LOS) to interact with TLR4 and promote activation.

Conditioned medium from insect cells inoculated with baculovirus encoding either wild-type (wt) or mutant C95Y MD-2, but not conditioned control medium, contained a polyhistidine-tagged protein that migrated with a size appropriate to that reported for MD-2 ($M_r$~20,000; (Shimazu et al., 1999) (FIG. 1A, 1B). In the absence of added conditioned medium, HEK/TLR4 cells were not activated by [$^{14}$C]-LOS aggregates+/−LBP and sCD14 or by the isolated [$^{14}$C-]LOS-sCD14 complex (FIG. 1C). However, addition of dialyzed conditioned medium from cells expressing wt MD-2 with [$^{14}$C]-$LOS_{agg}$+LBP and sCD14 or with purified [$^{14}$C]-LOS-sCD14 alone resulted in robust activation of HEK/TLR4 (FIG. 1C). There was little or no activation of these cells when wt MD-2 was added with $LOS_{agg}$+/−LBP but without sCD14. Parental HEK cells (TLR4$^-$) were not activated by endotoxin under any of the conditions tested (data not shown). Thus, activation of HEK293 cells by LOS required the concerted action of LBP, sCD14 (to produce LOS-sCD14), MD-2 and TLR4. The effects of the conditioned medium containing wt MD-2 were not seen with control conditioned medium (not shown) or medium containing C95Y MD-2 (FIG. 1C) even when added at 100× greater amounts (FIG. 1D). Maximum cell activation was produced with as little as 30 ng wt MD-2/ml added.

FIG. 1 depicts the expression and bioactivity of recombinant MD-2-$His_6$. FIGS. 1A and 1B depict SDS-PAGE immunoblots of control culture medium (FIG. 1A, lane 1) or medium from HiFive cells infected with recombinant baculovirus encoding wt (FIG. 1A, lane 2; FIG. 1B, lanes 1–3) or C95Y MD-2 (FIG. 1B, lane 4). MD-2 was detected using anti-$(His)_4$ antibody. All samples represent 1 μl of culture medium except B, lanes 2 and 3, which represent 0.3 and 0.1 μl and A, lane 3, which represents molecular weight markers. In FIG. 1C, HEK/TLR4 cells were incubated in HEPES-buffered HBSS+/0.1% albumin with [$^{14}$C]-$LOS_{agg}$ (3 ng/ml)+/−LBP (30 ng/ml) and/or (60 μl) culture medium containing wt MD-2 (MD-2) (open bars); $LOS_{agg}$+LBP and sCD14 (250 ng/ml)+/−wt (closed bars) or C95Y "MD-2" (striped bars), or [$^{14}$C]-LOS-sCD14 (2 ng LOS/ml)+/−wt or C95Y "MD-2" (closed bars). After overnight incubation, extracellular IL-8 was assayed by ELISA. In FIG. 1D, HEK/TLR4 cells were incubated with increasing amounts of wt (■) or C95Y (○) MD-2+[$^{14}$C]-LOS-sCD14 (2 ng/ml) and cell activation measured. Results shown are from one experiment (duplicate samples) representative of four independent experiments.

Formation and Function of a Novel Endotoxin-MD-2 Complex

There is a close correlation between the bioactivity of endotoxin and changes in the physical state of endotoxin induced by reversible protein associations. Since incubation of wt MD-2 with [$^{14}$C]-LOS-sCD14 is necessary for activation of HEK/TLR4 cells (FIG. 1C, 1D), the result of incubation of wt MD-2 with [$^{14}$C]-LOS-sCD14 at concentrations of wt MD-2 and LOS comparable to that used in the bioassays (FIG. 1) was examined by gel filtration. Treatment of [$^{14}$C]-LOS-sCD14 with wt MD-2 efficiently generated a new [$^{14}$C]-LOS-containing complex that eluted as $M_r$~25,000 on Sephacryl S100 (FIG. 2A). In contrast, treatment of [$^{14}$C]-LOS-sCD14 with the non-functional C95Y MD-2 produced no change in the chromatographic behavior of [$^{14}$C]-LOS-sCD14 (FIG. 2A). Re-chromatography of the peak fraction(s) from preparative generation of this new [$^{14}$C]-LOS-containing complex (FIG. 2B) yielded a single, symmetrical peak (recovery>90%+/−albumin, FIG. 2B). This complex is fully resolved by the gel filtration system from albumin and any residual [$^{14}$C]-LOS-sCD14 or sCD14 released from LOS-sCD14 during formation of the new complex. The isolated $M_r$~25,000 complex activated HEK/TLR4 cells in a potent dose, and TLR4-dependent manner (FIG. 2C); half-maximal activation occurred at approx. 150 pg [$^{14}$C]-LOS/ml (30 pM). Cell activation did not require addition of sCD14 or albumin (data not shown).

The apparent size of this active complex, as judged by gel sieving chromatography was consistent with a monomeric complex of LOS-MD-2. To determine if the [$^{14}$C]-LOS in this active complex was linked to MD-2, the ability of nickel charged agarose resin (HisBind) to co-capture polyhistidine-tagged MD-2 and [$^{14}$C]-LOS was examined. Both MD-2 and [$^{14}$C]-LOS adsorbed to the HisBind resin and were eluted with 200 mM imidazole (FIG. 2D, 2E). The low adsorption of [$^{14}$C]-LOS-sCD14 confirmed that the binding to the HisBind resin of [$^{14}$C]-LOS in the bioactive $M_r$~25,000 complex was specific and reflected its association with MD-2. Thus, treatment of [$^{14}$C]-LOS-sCD14 with soluble MD-2 generated an apparently monomeric [$^{14}$C]-LOS-MD-2 complex that activated HEK/TLR4 cells in a potent (pg/ml) dose- and TLR4-dependent manner independent of CD14. Also generated was a [$^{3}$H]-LPS-MD-2 complex from [$^{3}$H]-LPS purified from *E. coli* LCD25 (Munford et al., 1992) with chromatographic and functional properties virtually identical to [$^{14}$C]-LOS-MD-2 (data not shown).

Figure 2:
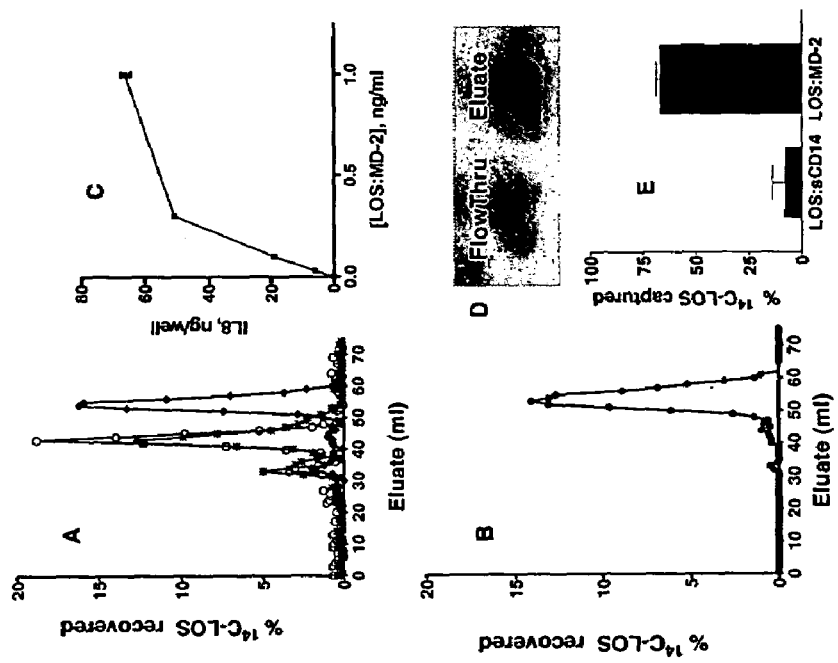
FIG. 2 depicts a bioactive complex containing MD-2 and [$^{14}$C]-LOS.

In FIG. 2, a bioactive complex ($M_r$~25,000) containing MD-2 and [$^{14}$C]-LOS is formed by incubation of [$^{14}$C]-LOS-sCD14 with wt, but not C95Y, MD-2. In FIG. 2A, dialyzed control insect cell medium (○) or medium containing wt (◆) or C95Y (✱) MD-2 was incubated for 30 min, 37° C. with (1:1 vol/vol) [$^{14}$C]-LOS-sCD14 in HBSS+, 10 mM HEPES and chromatographed on Sephacryl S100. Column fractions were analyzed for [$^{14}$C]-LOS. Identical results were obtained in analytical (5 ng [$^{14}$C]-LOS/ml+200 μl culture medium) or more preparative runs (reagents concentrated 20×). In FIG. 2B, peak fractions ($M_r$~25,000) from treatment of [$^{14}$C]-LOS-sCD14 with wt MD-2 (FIG. 2A) were re-chromatographed on S100 in HBSS+, 10 mM HEPES without HSA; recovery of [$^{14}$C]-LOS was >80%. In FIG. 2C, HEK (□) or HEK/TLR4 (■) were incubated overnight with the indicated amounts of LOS added as purified $M_r$~25,000 (LOS-MD-2) complex. Cell activation was measured by IL-8 accumulation. Results shown correspond to one experiment, in duplicate, representative of three similar experiments. FIGS. 2D and 2E depict adsorption and elution of bioactive $M_r$~25,000 complex to HisBind resin. Peak fractions of the purified complex (FIG. 2B; 10 ng [$^{14}$C]-LOS) were dialyzed against PBS and incubated with HisBind resin (0.125 ml) for 1 hr at 25° C. and processed as described in Methods. Non-adsorbed (Flow-thru) and adsorbed material eluted with 200 mM imidazole were precipitated with trichloroacetic acid to concentrate sample for SDS-PAGE/immunoblot analysis. As shown in FIG. 2D, alternatively, absorbed material was eluted with 2% SDS and counted by liquid scintillation spectroscopy. In FIG. 2E, adsorption of [$^{14}$C]-LOS-sCD14 was tested as a negative control. Overall recovery of [$^{14}$C]-LOS was greater than 90%. Results shown are the mean or representative of two closely similar experiments.

Efficient Formation of Bioactive Endotoxin-MD-2 Complex Requires Monomeric Endotoxin-CD14 Complex The demonstration that [$^{14}$C]-LOS-sCD14 could activate HEK/TLR4 cells by first transferring [$^{14}$C]-LOS to MD-2 indicated that it was this step that required presentation of endotoxin as a monomeric complex with CD14. Various presentations of [$^{14}$C]-LOS (i.e., [$^{14}$C]-LOS$_{agg}$+/−LBP, +/−sCD14) were compared for their ability to react with MD-2 to form the LOS-MD-2 complex (assessed by gel filtration chromatography) and subsequently activate HEK/TLR4 cells. Only $^{14}$C-LOS-sCD14 (either purified or generated during incubation of [$^{14}$C]-LOS$_{agg}$ with LBP and sCD14) was able to react with MD-2 to produce [$^{14}$C]-LOS-MD-2 and activate HEK/TLR4 cells (Table 1). These findings directly demonstrate the role of CD14 (i.e., endotoxin-CD14) in the delivery of endotoxin to MD-2 and demonstrate CD14 is not part of the complex that directly activates TLR4.

TABLE 1

Ability of various forms of [$^{14}$C]-LOS +/− proteins to form LOS-MD-2 and to activate HEK/TLR4.

| Materials | LOS-MD-2 | Activation |
|---|---|---|
| LOS$_{agg}$ + LBP | − − − | − − − |
| LOS$_{agg}$ + LBP, MD-2 | − − − | − − − |
| LOS$_{agg}$, LBP, sCD14 | − − − | − − − |
| LOS$_{agg}$, LBP, sCD14, MD-2 | + + + | + + + |
| LOS-sCD14 | − − − | − − − |
| LOS-sCD14 + MD-2 | + + + | + + + |
| LOS-sCD14 + Conditioned Culture media (No MD-2) | − − − | − − − |

Purified [$^{14}$C]-LOS$_{agg}$ or [$^{14}$C]-LOS-sCD14 (3 ng LOS/ml)+/−indicated proteins (30 ng/ml LBP, 250 ng/ml sCD14, 60 μl culture medium) were incubated at 37° C. for 30 min. After this incubation, samples were analyzed by gel filtration chromatography to monitor formation of [$^{14}$C]-LOS-MD-2 and by incubation with HEK/TLR4 cells to measure cell activation.

Molecular Requirements for MD-2 Dependent Delivery of Endotoxin

Figure 3:
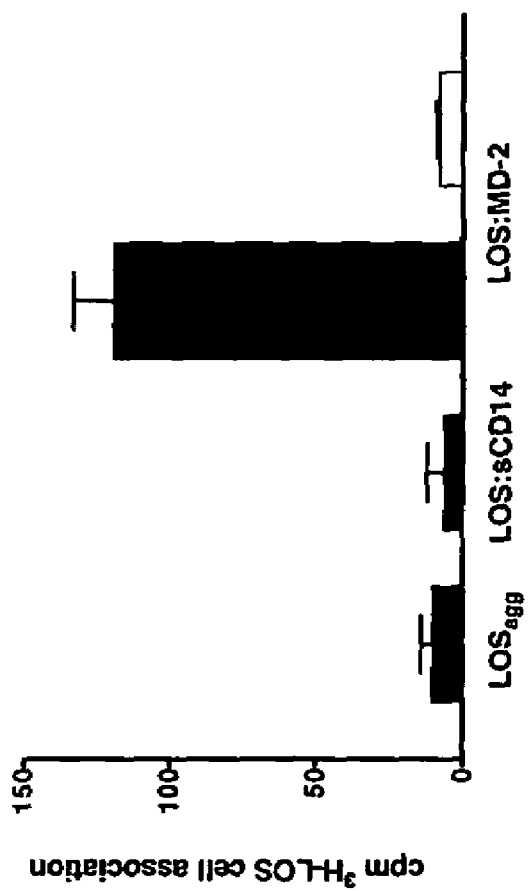
FIG. 3 depicts amounts of [$^3$H]-LOS associated with cells.

Table 1 also indicates that endotoxin must be presented in the form of a monomeric endotoxin-MD-2 complex to activate HEK/TLR4 cells. This could reflect a unique ability of MD-2 to deliver endotoxin to TLR4. To test this hypothesis, cell association of purified LOS$_{agg}$, LOS-sCD14 or LOS-MD-2 complexes to parental and HEK/TLR4 cells were compared. Initial experiments with [$^{14}$C]-LOS did not reveal significant cell association of radiolabeled LOS under any condition. These negative results could simply reflect the limited amount of surface TLR4 available and needed to engage LOS-MD-2 for cell activation. To address this, LOS was isolated after metabolic labelling with [³H]-acetate to achieve nearly 10-fold higher specific radioactivity (~4000 cpm/ng) and generated [³H]-Los$_{agg}$ and protein: [³H]-LOS complexes. Using the [³H]-LOS, specific TLR4-dependent cell association of [³H]-LOS-MD-2 only, with virtually no TLR4-independent cell association of LOS-MD-2, was readily detected (FIG. 3). In addition, no cell association of either [³H]-LOS$_{agg}$ or [³H]-LOS-sCD14 to HEK cells±TLR4 was detected (FIG. 3).

FIG. 3 depicts delivery of [³H]-LOS-MD-2 but not [³H]-LOS$_{agg}$ or [³H]-LOS-sCD14 to HEK/TLR4. HEK (□) or HEK/TLR4 (■) cells were incubated with [³H]-LOS (0.75 ng/ml) in the form of LOS$_{agg}$, LOS-sCD14, or LOS-MD-2. After overnight incubation at 37° C., cells were washed and lysed as described in Methods. The amount of [³H]-LOS associated with the cells was measured by liquid scintillation spectroscopy. Results are from one experiment in duplicate, representative of three similar experiments.

These findings indicate a bifunctional role for MD-2, coupling endotoxin recognition to TLR4 activation. If simultaneous engagement of endotoxin and TLR4 by MD-2 is required for TLR4-dependent cell activation by endotoxin, the presence of a stoichiometric excess of MD-2 relative to TLR4 should inhibit cell activation by endotoxin. To test this hypothesis, the effect of adding varied amounts of conditioned insect cell culture medium containing wt, C95Y, or no MD-2 was examined. Addition of medium containing wt MD-2, but not control medium, produced a dose-dependent inhibition of the activation of HEK/TLR4 by [¹⁴C]-LOS-MD-2 (FIG. 4A). Medium containing C95Y MD-2 had an intermediate inhibitory effect consistent with the (partial) retention of TLR4 binding by this mutant MD-2 species. Inhibitory effects of added MD-2 had no direct effect on LOS-MD-2 (FIG. 4B, no change in chromatographic behavior), but blocked TLR4-dependent cell association of [³H]-LOS-MD-2 (FIG. 4C). This is consistent with a need for simultaneous engagement of endotoxin and TLR4 by individual molecules of MD-2 for TLR4-dependent cell activation. Thus, depending on levels of expression, MD-2 can have inhibitory as well as stimulatory effects on TLR4-dependent cell activation by endotoxin.

Figure 4:
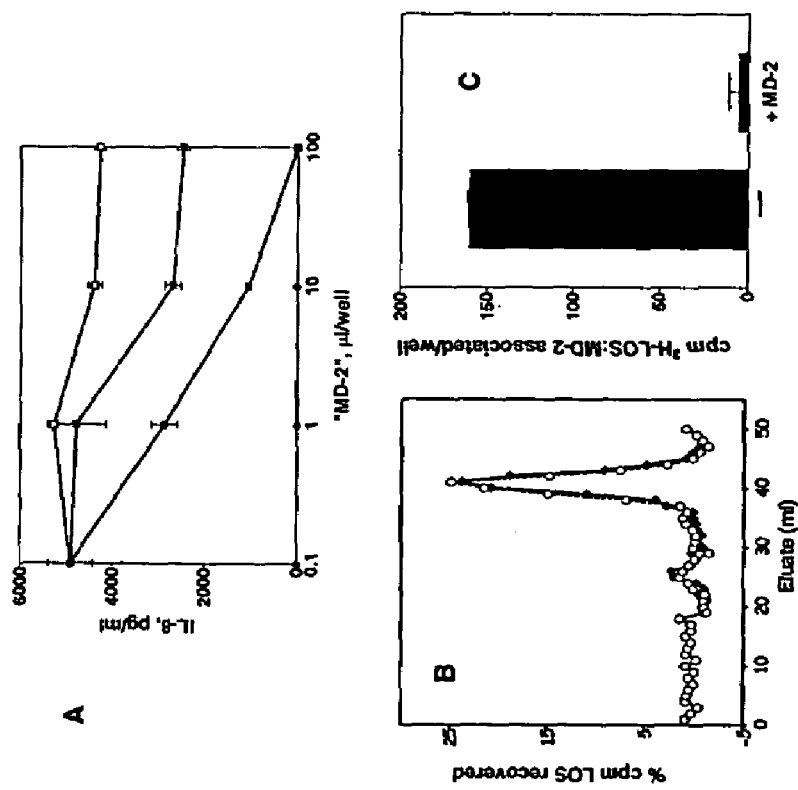
FIG. 4 depicts effects of added MD-2 on activation of HEK/TLR4 by [$^3$H]-LOS-MD-2 and delivery of [$^3$H]-LOS-MD-2 to HEK/TLR4.
Figure 5:
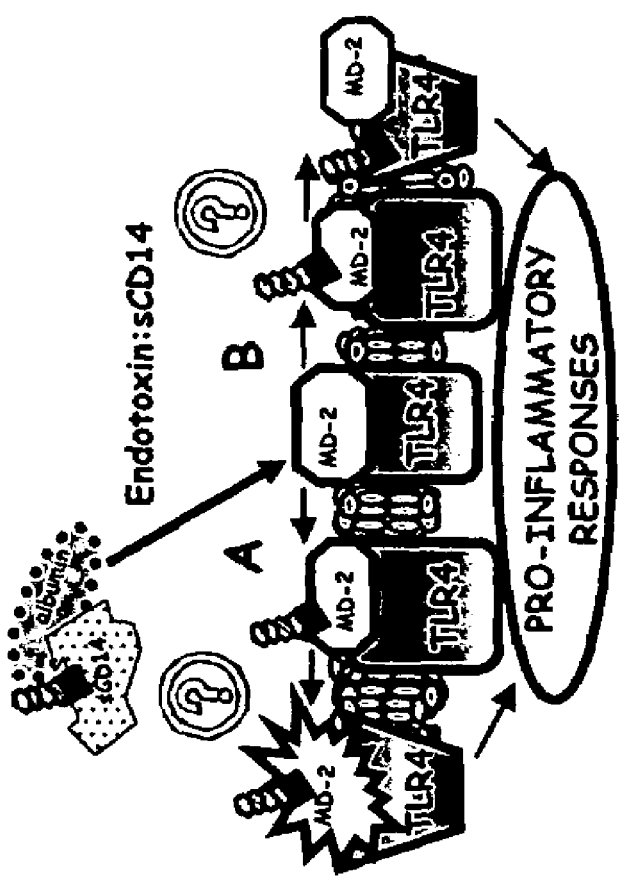
FIG. 5 depicts mechanisms of action of MD-2 in endotoxin-dependent activation of TLR4.

FIG. 4 depicts the effects of added MD-2 on activation of HEK/TLR4 by [³H]-LOS-MD-2 and delivery of [³H]-LOS-MD-2 to HEK/TLR4. In FIG. 4A, cells were incubated in HBSS+, 10 mM HEPES/0.1% albumin with [¹⁴C]-LOS-MD-2 (0.3 ng/ml) and increasing amounts of wt (■), C95Y (✱) MD-2 or negative control medium (□) as well as with wt MD-2 but no [¹⁴C]-LOS-MD-2 (○). After overnight incubation, extracellular accumulation of IL-8 was measured. The concentrated and dialyzed conditioned media contained ca. 10 ng (wt or C95Y) MD-2/μl. Results are from one experiment in duplicate, representative of three similar experiments. In FIG. 4B, purified [¹⁴C]-LOS-MD-2 (1 ng/ml) was pre-incubated +(●) or −(○) an amount of MD-2 that completely inhibited activation (40 μl of 20-fold concentrated and dialyzed conditioned media) for 30 min, 37° C. in HBSS+, 10 mM HEPES before chromatography on Sephacryl S200. Column fractions were analyzed for [¹⁴C]-LOS by liquid scintillation spectroscopy. In FIG. 4C, [³H]-LOS-MD-2 (0.75 ng/ml; ca. 3000 cpm)+/−excess MD-2 as indicated in B was incubated with HEK/TLR4 cells overnight at 37° C. as described in Methods. After supernatants were removed, cells were washed and then lysed as described in Methods. The amount of radioactivity associated with the cells was determined by liquid scintillation spectroscopy. No radioactivity was associated with parental cells.

Materials and Methods

LBP and sCD14 were provided by Xoma (US) LLC. (Berkeley, Calif.). Both parental HEK293 and cells stably transfected with TLR4 (HEK/TLR4) were provided by Dr. Jesse Chow, Eisai Research Institute, (Andover, Mass.). Chromatography matrices and electrophoresis supplies were purchased from Amersham Biosciences (Piscataway, N.J.). Human serum albumin was obtained as an endotoxin-free, 25% stock solution (Baxter Healthcare Corp., Glendale, Calif.). [¹⁴C]-LOS or [³H]-LOS was isolated from an acetate auxotroph of *Neisseria meningitidis* Serogroup B after metabolic labeling and isolated as previously described (28). [¹⁴C or ³H]-LOS$_{agg}$ (apparent M$_r$>20 million) and [¹⁴C or ³H]-LOS-CD14 (M$_r$~60,000) were purified as previously described(21, 28). [³H]-LPS from *E. coli* LCD25 was purchased from List Biologicals (Campbell, Calif.) as processed as described previously (Iovine et al., 2002).

Preparation of Recombinant MD-2

MD-2 cDNA was isolated, linearized, and inserted, using NcoI and XhoI-sensitive restriction sites, into the baculovirus transfection vector pBAC11(Novagen) that provides a six residue polyhistidine tag at the carboxyl terminal end of MD-2 and 5' flanking signal sequence (gp64) to promote secretion of the expressed protein. DNA encoding each desired product was sequenced in both directions to confirm fidelity of the product. Production and amplification of recombinant viruses were undertaken in collaboration with the Diabetes and Endocrinology Research Center at the Veterans' Administration Medical Center, Iowa City, Iowa. Sf9 cells were transfected with linear baculovirus DNA and the pBAC 11 vector using Bacfectin, according to a procedure described by Clontech. For production of recombinant protein, HiFive cells (Invitrogen) were incubated in serum-free medium and inoculated at an appropriate virus titer. Supernatants were collected and dialyzed either against HEPES-buffered (10 mM, pH 7.4) Hanks' balanced salts solution with divalent cations (HBSS⁺), pH 7.4 or 50 mM phosphate, 150 mM NaCl, pH 7.4 (PBS). To absorb the expressed polyhistidine tagged protein, nickel charged agarose resin (HisBind, Novagen, Madison, Wis.) was incubated batchwise with culture medium pre-dialyzed against PBS containing 5 mM imidazole. After extensive washing with this same buffer, adsorbed material was eluted with 200 mM imidazole. Flow-through and eluate fractions were analyzed by immunoblot as described below. The presence of [¹⁴C-LOS] was evaluated by liquid scintillation spectroscopy.

Immunoblotting

To detect polyhistidine labeled wt and C95Y MD-2, an anti-polyhistidine antibody (Tetra-His antibody, Qiagen, Valencia, Calif.) was used. Samples were electrophoresed using an Amersham Biosciences PhastGel System (10–15% gradient acrylamide gel) and transferred to nitrocellulose by semi-dry transfer. The nitrocellulose was washed with Tris-buffered saline (TBS), pH 7.5, containing 0.05% Tween-20 and 0.2% TritonX-100 (TBSTT), blocked to reduce nonspecific background with 3% BSA in TBSTT for 1 hr at 25° C., and incubated with the anti-His$_4$ antibody in TBSTT overnight. After washing with TBSTT, the blot was incubated with donkey anti-mouse IgG conjugated to horseradish peroxidase (BioRad) for 1 hr at 25° C. in TBS containing 3% goat serum and washed with TBSTT exhaustively. Blots were developed using the Pierce SuperSignal substrate system.

HEK Cell Activation Assay

HEK cells+/−TLR4 have been extensively characterized and were cultured as has been described (Yang et al., 2000). For cell activation assays, cells were grown to confluency in 48 well plates. Cell monolayers were washed with warm PBS 2× and incubated overnight at 37° C., 5% $CO_2$, and 95% humidity in HBSS+, 0.1 % HSA with the supplements indicated in the legends to FIGS. 1–3 and Table 1. Activation of HEK cells was assessed by measuring accumulation of extracellular IL-8 by ELISA as previously described (Denning et al., 1998).

Chromatography

Columns of Sephacryl HR S200 (1.6 cm×30 cm) or S100 (1.0 cm×60 cm) were pre-equilibrated in 10 mM HEPES, HBSS+/−0.1% HSA. Aliquots containing [$^{14}$C]-$LOS_{agg}$+/−LBP, +/−sCD14, +/−dialyzed conditioned insect cell medium or [$^{14}$C]-LOS-sCD14+/−dialyzed conditioned insect cell medium or [$^{14}$C]-LOS-MD-2 were incubated at 37° C., 30 min before gel filtration chromatography. Fractions (1 ml) were collected (flow rate: 0.5 ml/min) at room temperature using an Amersham Biosciences AKTA FPLC. Samples for chromatography contained from 2 ng to 200 ng [$^{14}$C]-$LOS_{agg}$, [$^{14}$C]-LOS-sCD14 or [$^{14}$C]-LOS-MD-2 in 1 ml of column buffer+/−0.1 % HSA. Aliquots of the collected fractions were analyzed by liquid scintillation spectroscopy using a Beckman LS liquid scintillation counter to detect [$^{14}$C]-LOS. Recoveries of [$^{14}$C]-LOS were >70%+/−albumin. All solutions used were pyrogen-free and sterile-filtered. After chromatography, selected fractions to be used in bioassays were pooled and passed through sterile syringe filters (0.22 μm) with greater than 90% recovery of radiolabeled material in the sterile filtrate. Fractions were stored under sterile conditions at 4° C. for more than 3 months with no detectable changes in chromatographic or functional properties. Columns were calibrated with BioRad gel filtration standards that included thyroglobulin ($V_o$), γ-globulin, ovalbumin, myoglobin, and vitamin B12 ($V_t$) and human serum albumin. Experiments utilizing [$^3$H]-LOS and [$^3$H]-LPS were carried out by the same procedure.

Cell Association of Various Forms of Endotoxin

HEK or HEK/TLR4 cells were grown to confluency in 6 well plates, washed twice with warm PBS, and [$^3$H]-LOS aggregates or [$^3$H]-LOS-protein complexes+/−indicated supplements were incubated overnight at 37° C., 5% $CO_2$, and 95% humidity in DMEM, 0.1% HSA with the supplements indicated in the legends to FIGS. 3 and 4. After the incubation, supernatants (extracellular media) were collected, cells were washed twice with cold PBS, and cells were lysed and solubilized using RNeasy lysis buffer (Qiagen). The amount of radioactivity associated with the cells was determined by liquid scintillation spectroscopy. Total recovery of radioactivity was >90%.

EXAMPLE 2

The results presented herein demonstrate that in well-differentiated primary cultures of human airway epithelia TLR4, but little or no MD-2, is expressed. These cells are relatively unresponsive to added endotoxin even in the presence of LBP and CD14. However, the responsiveness of these cells to endotoxin is markedly amplified by either the endogenous expression or the exogenous addition of MD-2, indicating that the constitutively low levels of MD-2 expression in these cells at "rest" is important in maintaining their hypo-responsiveness to endotoxin. Changes in MD-2 expression in the airway epithelium and/or neighboring cells can be achieved by exposure of these cells to specific bacterial and host products and can thereby regulate airway responsiveness to endotoxin.

Human Airway Epithelia are Hyporesponsive to Applied Endotoxin

Nontypeable *Haemophilus influenza* (NTHi) is a common commensal, and sometimes a pathogen, of the respiratory tract (Lerman et al., 1979; Smith et al., 1989; Bandi et al., 2001). The experiments described herein explored whether endotoxin (LOS) from NTHi increased HBD-2 expression after application to the apical surface of human airway epithelia. As shown in FIGS. 6A and 6B, following the apical application of LOS in the presence of sCD14 and LBP, there was little or no change in the HBD-2 MRNA abundance. In contrast, IL-1β stimulated a large increase in HBD-2 expression (>10,000-fold).

Figure 6:
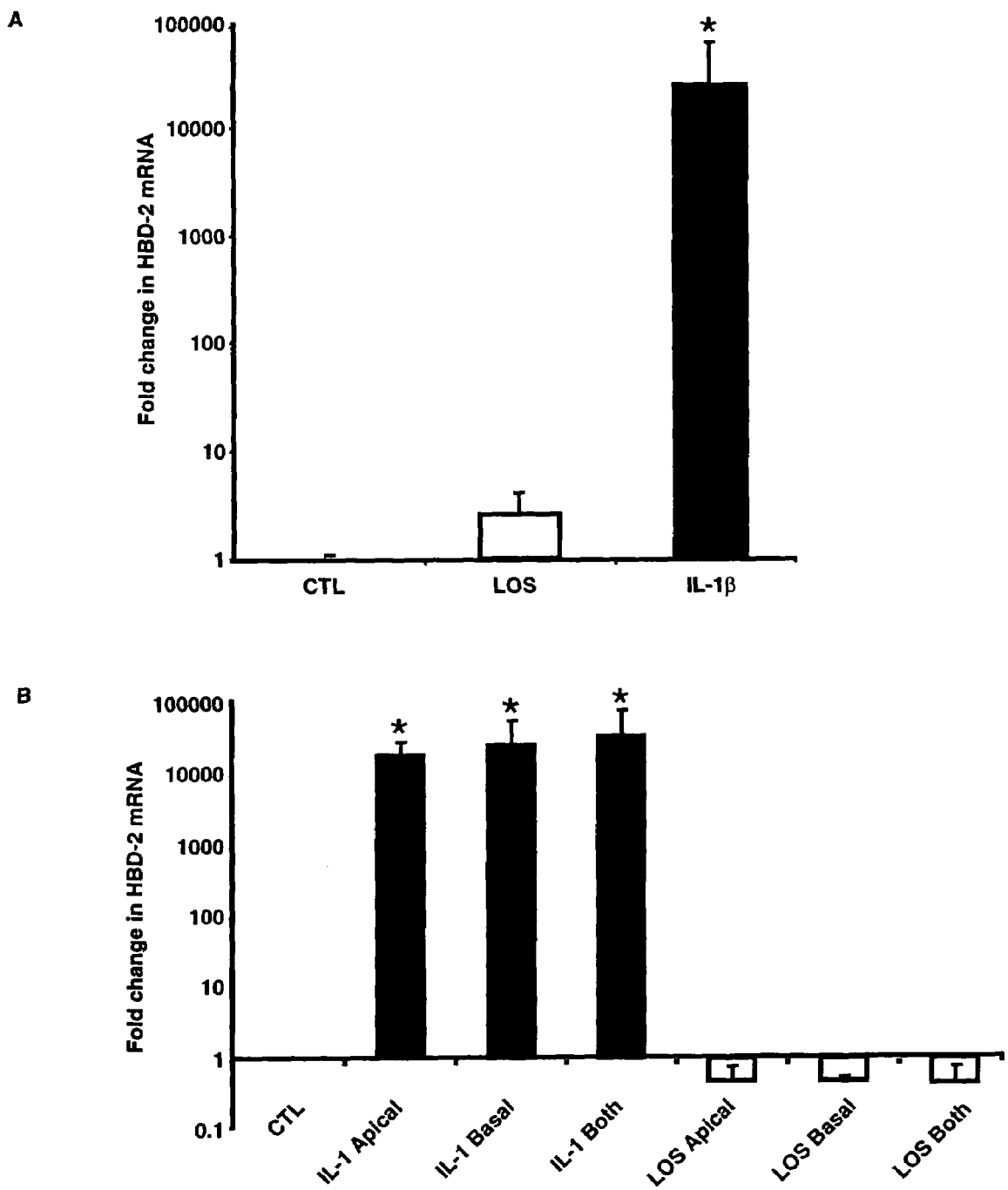
FIG. 6 depicts endotoxin responsiveness of well-differentiated primary cultures of human airway epithelia.

FIG. 6 depicts endotoxin responsiveness of well-differentiated primary cultures of human airway epithelia. Polarized epithelia were treated with NTHi LOS (100 ng/ml), sCD14 (100 ng/ml) and LBP (250 ng/ml) by apical application in a 50 μl volume. Twenty-four hours later, epithelia were harvested and analyzed for HBD-2 mRNA expression by real time PCR. As depicted in FIG. 6A, apical stimulation of airway epithelia with NTHi LOS induced little change in HBD-2 MRNA expression (2 epithelia/trial, n=3 different donors, * indicates p<0.05). In contrast, IL-1β markedly induces HBD-2 mRNA. FIG. 6B depicts the polarity of epithelial responses to IL-1β and NTHi LOS. Reagents were applied to the apical, basolateral or both surfaces as indicted in the same concentrations as in FIG. 6A. IL-1β induced HBD-2 expression from either surface, while NTHi LOS failed to induce responses from either side. Results represent replicate data from 2 different specimens, * indicates p<0.05.

It was possible that the striking lack of responsiveness of airway epithelia to endotoxin alone reflected a polar distribution of receptors for endotoxin on the basolateral surface of airway epithelia. To address this possibility, NTHi LOS was applied to either the apical or basolateral surface of airway epithelia and HBD-2 expression quantified by real time PCR. As shown in FIG. 6B, neither the apical or basolateral application of LOS in the presence of sCD14 and LBP caused significant induction of HBD-2 MRNA expression. In contrast, IL-1β application to either or both sides of the epithelium again induced robust HBD-2 expression. These results indicate that human airway epithelia are relatively hypo-responsive to endotoxin.

MD-2 Expression in Human Airway Epithelia Enhances Endotoxin Responsiveness

Pattern recognition receptors from the family of Toll-like receptors (TLRs) play a central role in the recognition of bacterial products, including endotoxin from Gram-negative bacteria (Medzhitov et al., 2000). TLR4 is a key receptor for recognition and signaling in response to endotoxin (Medzhitov et al., 1997) and optimal responses require presentation of the bacterial product in the presence of LBP, CD14, and MD-2 (Shimazu et al., 1999; Gioannini et al., 2003; and Abreu et al., 2001). Human airway epithelia were screened for the expression of TLR4, CD14 and MD-2 mRNAs using RT-PCR. Alveolar macrophages served as a positive control. FIG. 7 demonstrates that airway epithelia express the mRNAs for TLR4 and CD14. However, while macrophages demonstrated an MD-2 signal, no significant MD-2 transcripts were detected in airway epithelia following 35 cycles of PCR.

FIG. 7 depicts expression of components of innate immune signaling in human airway epithelia (HAE). Primary cultures of human airway epithelia were screened for expression of CD14, TLR4, MD-2 and GAPDH as described in Methods below using RT-PCR (35 cycles). Expression in epithelia was contrasted with that of human alveolar macrophages (Mac). RT=reverse transcriptase. Representative results from experiment performed in two different human specimens.

Figure 8:
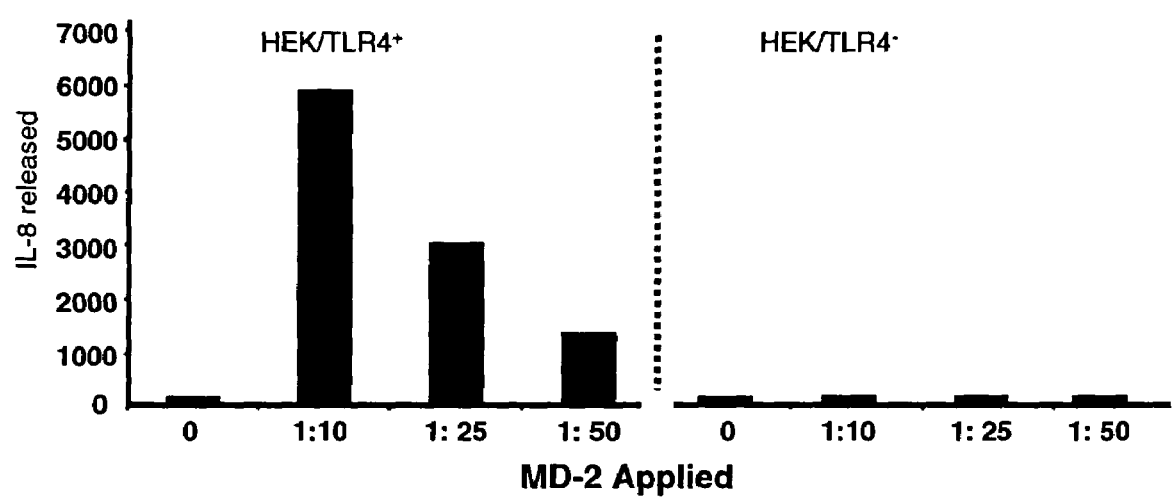
FIG. 8 depicts results indicating the generation of a functional adenoviral vector expressing human MD-2.

The apparent absence of MD-2 expression in primary cultures of human airway epithelia suggests that the failure of endotoxin to induce HBD-2 expression in these cells reflects a lack of available MD-2 and a resultant inability to form an optimal complex for TLR4-dependent signaling. To address this hypothesis, the deficiency of MD-2 in airway epithelia was circumvented by using an adenoviral vector containing the human MD-2 cDNA. To demonstrate that the Ad-MD-2 construct directed expression of functional MD-2 protein, the vector was first used to transduce parental HEK293 cells. Conditioned medium recovered from the transduced cells were then assayed for the presence of active MD-2 by measuring activation of HEK293 cells±TLR4 by added LOS-sCD14 (the bioactive product of LBP/sCD14 treatment of LOS; (Giardina et al., 2001; Gioanniniet al., 2002; and Gioannini et al., 2003)). As shown in FIG. 8, conditioned medium from Ad-MD-2 transduced cells produced a dose-dependent augmentation of IL-8 release by HEK/TLR4$^+$ cells but not the parental (TLR4$^-$) cells, consistent with the functional expression of MD-2 by the vector.

FIG. 8 depicts results indicating the generation of a functional adenoviral vector expressing human MD-2. A replication incompetent adenoviral vector expressing MD-2 was used to infect 293 cells with an MOI of 50. 24 hr later, cell culture supernatants were harvested and applied to HEK cells+/−TLR4 in dilutions as indicated in the presence of LOS-sCD14 complexes (2 ng LOS/ml) to stimulate TLR4 signaling (IL-8 production by ELISA). Results demonstrate that the adenoviral vector directs production of MD-2 that is secreted and functional. TLR4$^-$ cells showed no significant response to LOS-sCD14±medium containing MD-2.

Transduction of the human airway epithelial cells with Ad-MD-2, but not with the control Ad-vector, markedly increased the cellular levels of MD-2 MRNA (data not shown). Importantly, the Ad-MD-2 complemented epithelia exhibited markedly enhanced endotoxin responsiveness following apical application of either purified LOS aggregates+ LBP and sCD14 (FIG. 9A) or purified LOS-sCD14 (FIG. 9C)

LOS-induced increases in HBD-2 mRNA were paralleled by increased secretion of HBD-2 peptide (data not shown) and increased NF-κB luciferase activity in MD-2 complemented cells (FIG. 9B). In contrast, basolateral application of LOS to Ad-MD-2 complemented epithelia failed to elicit significant NF-κB signaling or induction of HBD-2 expression (n=2, data not shown). These results indicate that the expression of MD-2 in airway epithelia confers endotoxin (LOS) responsiveness. Conversely, in the absence of MD-2, surface epithelia are relatively unresponsive to apical or basolateral endotoxin stimulation.

Figure 9:
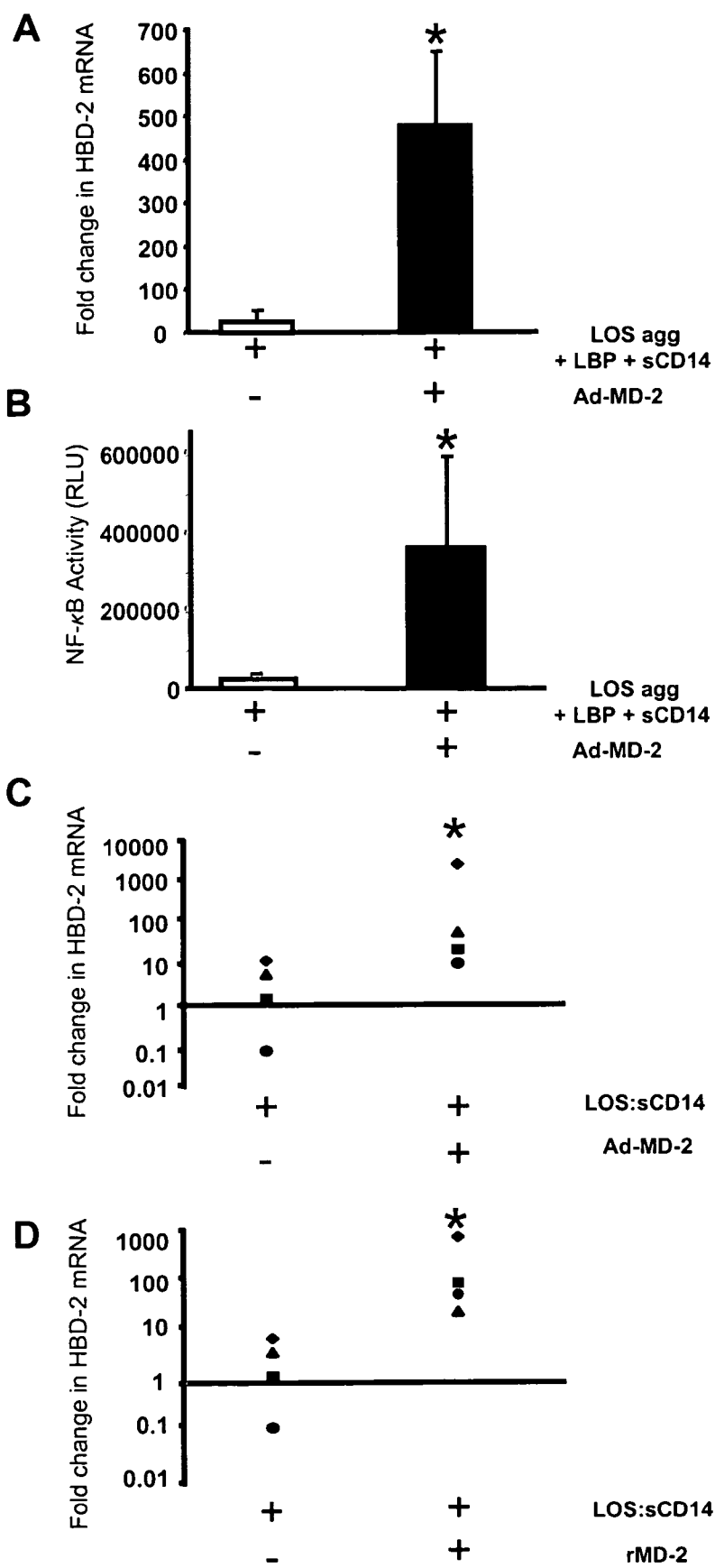
FIG. 9 depicts the effects of MD-2 complementation on endotoxin responsiveness in human airway epithelia.

FIG. 9 depicts the effects of MD-2 complementation on endotoxin responsiveness in human airway epithelia. FIG. 9A depicts results indicating that Ad-MD-2 complementation of well-differentiated polarized human airway epithelia confers enhanced responsiveness to NTHi LOS as measured by HBD-2 MRNA expression. Cells were treated with LOS, sCD14 and LBP with or without pretreatment with an adenoviral vector expressing MD-2 as described in Methods below. Fold increase in HBD-2 mRNA expression were quantified by real time PCR. Results were normalized to control level of HBD-2 expression in untreated cells set at 1. Representative figure from three human specimens; * indicates p<0.05. FIG. 9B depicts results indicating that MD-2 complementation confers enhanced responsiveness to endotoxin as measured by NF-κB-luciferase activity. LOS stimulation protocol was same as described in 9A. NF-κB-luciferase activity was measured 24 hr following endotoxin treatment (n=5 epithelia/condition, * indicates p<0.05). FIG. 9C depicts results indicating that complementation of airway epithelia with Ad-MD-2 protein confers enhanced responsiveness to LOS-sCD14 complexes. Well differentiated human airway epithelia were treated with *N. meningitidis* LOS-sCD14 (5 ng LOS/ml), with or without Ad-MD-2 pre-treatment. 24 hr after endotoxin treatment, HBD-2 expression was quantified by real time PCR. Results shown represent findings from four different human airway specimens. Symbols represent data from individual human specimens; * indicates p<0.05.

Extracellular Complementation with Recombinant MD-2 Protein Enhances Endotoxin Signaling in Human Airway Epithelia Genetically manipulated cells such as the HEK/TLR4$^+$ cells have been used to show that endogenous (co-) expression of MD-2 or addition of secreted MD-2 to TLR4$^+$/MD-2$^-$ cells confers increased endotoxin responsiveness. The primary cultures of human airway epithelia provide a more natural setting to test the effect of exogenous addition of recombinant MD-2 (rMD-2) on cellular responsiveness to endotoxin (i.e., LOS-sCD14). As shown in FIG. 9D, addition of conditioned insect cell culture medium containing rMD-2 increased the response of the human airway epithelial cultures to LOS-sCD14 by ≧100-fold. Control conditioned medium, by contrast, had no effect (data not shown).

FIG. 9D depicts results indicating that complementation of airway epithelia with recombinant MD-2 protein (rMD-2) confers enhanced responsiveness to endotoxin. Well differentiated human airway epithelia were treated with *N. meningitidis* LOS-sCD14 (5 ng LOS/ml), with or without the addition of cell culture supernatants containing rMD-2. 24 hr after endotoxin treatment. HBD-2 expression was quantified by real time PCR. Results shown represent findings from four different human airway specimens. Symbols represent data from individual human specimens; * indicates p<0.05.

Expression of MD-2 in Airway Epithelia is Regulated by Pro-Inflammatory Stimuli

The demonstration that expression (or addition) of MD-2 could markedly increase the responsiveness of the airway epithelia to endotoxin prompted a search for more natural conditions in which endogenous MD-2 expression might be up-regulated. The effects of specific host or bacterial products on cellular MD-2 levels were examined. As shown in FIG. 10, real-time PCR demonstrated marked increases in steady state MD-2 MRNA levels following exposure of the apical surface of the cultured airway epithelium to heat killed NTHi, the NTHi outer membrane protein P6 or the combination of TNF-α and interferon gamma. The levels of MD-2 MRNA attained under these conditions were similar to that induced by phorbol myristate acetate but still significantly less than MD-2 mRNA levels in human alveolar macrophages. These findings demonstrate that, in response to specific stimuli, levels of MD-2 transcript can be up-regulated in human airway epithelia.

FIG. 10 depicts results indicating that MD-2 mRNA expression in human airway epithelia is inducible in response to several stimuli. Fold increase in MD-2 mRNA expression was quantified using real time PCR. FIG. 10 represents the results from three independent experiments on three different epithelial preparations. * indicates p<0.05.

Materials and Methods

Reagents

PMA, human recombinant IL-1β, TNF-α and INF-γ were obtained from Sigma (St Louis, Mo.). Soluble CD14 (sCD14) and LPS binding protein (LBP) were provided by Xoma (US) LLC (Berkeley, Calif.). Lipooligosaccharide (LOS) from non-typeable *Haemophilus influenzae* was isolated by a mini-phenol-water extraction procedure, as previously described (Inzana et al., 1997). LOS was also isolated from *Neisseria meningitidis* and used as purified aggregates (LOS agg) and as monomeric LOS-sCD14 complexes as previously described (Giardina et al., 2001; and Gioanniniet al., 2002). P6 from non-typeable *Haemophilus influenzae* was a generous gift from Dr. Timothy F. Murphy, SUNY, Buffalo. NTHi strain 12 (Frick et al., 2000) was a kind gift of Dr. Dwight Look.

Cell Culture

Primary cultures of human airway epithelia were prepared from trachea and bronchi by enzymatic dispersion using established methods (Karp et al., 2002). Briefly, epithelial cells were dissociated and seeded onto collagen-coated, semi-permeable membranes with a 0.4 µm pore size (Millicell-HA; surface area 0.6 $cm^2$; Millipore Corp., Bedford, Mass.). Human airway epithelial cultures were maintained in Ultroser G (USG) media at 37° C., 5% $CO_2$. Millicell inserts were placed into 24-well plastic cell culture plates (Costar, Cambridge, Mass.). Twenty-four hours after seeding, the mucosal medium was removed and the cells were allowed to grow at the air-liquid interface as reported previously (Karp et al., 2002). Only unpassaged, well-differentiated cultures (>2 weeks old) were used in these studies. The presence of tight junctions was confirmed by transepithelial resistance measurements using a volt-ohm meter (World Precision Instruments, Sarasota, Fla.; resistance >500 Ω·$cm^2$). This study was approved by the Institutional Review Board of the University of Iowa.

Isolation of Macrophages from Bronchoalveolar Lavage Fluid

Bronchoalveolar lavage fluid (BAL) was obtained from normal volunteers as previously reported (McCray et al., 1997). BAL was filtered through 2 layers of gauze and spun down at 3500 rpm at 4° C. for 5 min. The cell pellets were resuspended in 10 ml sterile saline and quantified using a Coulter counter. The study was approved by the Institutional Review Board of the University of Iowa.

Adenoviral Vector Constructs

A commercially available NF-κB-Luc plasmid (Clontech Laboratories Inc., Palo Alto, Calif.) was used as a template to generate a recombinant adenovirus vector (Ad-NF-κB-Luc). The fragment containing the firefly luciferase gene driven by four tandem copies of the NF-κB consensus sequence fused to a TATA-like promoter from Herpes simplex virus thymidine kinase gene was released by KpnI and XbaI double digestion. The fragment was inserted into a promoterless adenoviral shuttle plasmid (pAd5mcspA) and Ad-NF-κB-Luc virus was generated by homologous recombination as previously described and stored in 10 mM Tris with 20% glycerol at −80° C. (Anderson et al., 2000). The particle titer of adenoviral stock was determined by A260 reading. The functional titer of the adenoviral stock was determined by plaque titering on 293 cells and expression assays for the encoded protein.

An adenoviral vector expressing human MD-2 was generated. Total RNA was isolated from human alveolar macrophages using TRI Reagent (Molecular Research Center, Inc., Cincinnati, Ohio). RNA was reverse transcribed to generate cDNA using superscript II reverse transcriptase (Life Technologies, Rockville, Md.) following the manufacturer's protocol. PCR was employed to amplify a cDNA including the ORF of human MD-2 (Genbank AB018549). The primers consisted of forward-5'-CTTGTCGACATTTG-TAAAGCTTTGGAGATATTGAA-3' (SEQ ID NO:1) and reverse-5'-ATTGAATTCTAATTTGAATTAGGTTGGT-GTAGGA-3' (SEQ ID NO:2) (Shimazu et al., 1999). The reaction was performed at 95° C. for 5 min, followed by 35 cycles at 94° C. for 1 min, 60° C. for 1 min and 72° C. for 1 min. The chain reaction was elongated at 72° C. for 10 min. The fidelity of the PCR product was confirmed by DNA sequencing. The MD-2 cDNA was digested by SalI at the 5' end and EcoRI at the 3' end and then inserted into an adenoviral shuttle plasmid (pAd5cmcpA), containing the CMV promoter and Ad-MD2 virus was generated by homologous recombination. The titering and storage of the Ad-MD2 virus were identical to those described above for Ad-NF-κB-Luc. An adenoviral vector expressing the human TLR-4 cDNA was also used in these studies. The methods for the construction of this vector were published previously (Arbour et al., 2000).

Messenger RNA Analysis

Semiquantitative RT-PCR

RT-PCR was used to detect expression of TLR4, CD14 and MD-2 mRNA in human airway epithelia and alveolar macrophages. 1 µg of total RNA from each sample was reverse transcribed using random hexamer primers with SuperScript (GibcoBRL). First strand cDNA was amplified by PCR. The primer set for TLR4 consisted of forward-5'-TGAGCAGTCGTGCTGGTATC-3' (SEQ ID NO:3); reverse-5'-CAGGGCTTTTCTGAGTCGTC-3' (SEQ ID NO:4) and amplified a product of 166 bp. The primer set for CD14 consisted of forward-5'-CTGCAACTTCTCCGAAC-CTC-3' (SEQ ID NO:5) and reverse-5'-CCAGTAGCTGAG-CAGGAACC-3' (SEQ ID NO:6) and produced a cDNA fragment of 215 bp. The primer set for MD-2 included forward-5'-TGTAAAGCTTGGAGATATTGAA-3' (SEQ ID NO:7) and reverse-5'-TTTGAATTAGGTTGGTGTAGGA-3' (SEQ ID NO:8) and amplified a product of 508 bp. As a control for amplification, GAPDH was amplified in each reaction using the following primers-forward-5'-GT-CAGTGGTGGACCTGACC-3' (SEQ ID NO:9); reverse-5'-AGGGGTCTACATGGCAACTG-3' (SEQ ID NO:10). Each reaction contained approximately 1.25 pM of the primers, 3 mM $Mg^{2+}$. After an initial denaturing step (95° C. for 3 min), 35 cycles of denaturing (94° C. for 30 sec), annealing (60° C. for 30 sec), and extension (72° C. for 30 sec), followed by 5 min at 72° C. for elongation were conducted. PCR products were electrophoresed on a 2% agarose gel and visualized using ethidium bromide.

Real-Time Quantitative PCR for Detecting HBD-2 and MD-2

Real-time PCR was employed to detect human β-defensin-2 and MD-2 and to quantify changes in expression. Real-time quantitative PCR was performed using a sequence detector (ABI PRISM 7700, Applied Biosystems, Foster City, Calif.) and Taqman technology (Roche Molecular Diagnostic Systems) following the manufacturer's protocols (Bustin, 2000). The primers and probes were designed using the Primer Express program (Applied Biosystems). For MD-2, the primers were-forward5'-CAACAATATCAT-TCTCCTTCAAGGG-3' (SEQ ID NO:11), reverse 5'-GCATTTCTTCTGGGCTCCC-3' (SEQ ID NO:12), and probe 5'-AAAATTTTCTAAGGGAAAATACAAATGT-GTTGTTGAAGC-3' (SEQ ID NO:13). For HBD-2, the forward primer was-5'-CCTGTTACCTGCCTTAA-GAGTGGA-3' (SEQ ID NO:14), the reverse primer-5'-ACCACAGGTGCCAATTTGTTTA-3' (SEQ ID NO:15), and the probe was-5'-CCATATGTCATCCAGTCTTTTGC-CCTAGAAGG-3' (SEQ ID NO:16). Both probes contain a fluorescent reporter (6-Carboxyfluorescein [FAM]) at the 5' end and a fluorescent quencher (6-Carboxytetramethyl-rhodamine [TAMRA]) at the 3' end. As an internal control for normalization, human GAPDH real-time quantitative PCR was conducted in every reaction. The primers and probes were purchased from Roche Molecular Diagnostic Systems. The PCR fragments were amplified for 40 cycles (15 sec at 95° C. and 1 min at 60° C.).

Transduction of Human Airway Epithelia with Adenoviral Expression Vectors

Primary cultures of well-differentiated human airway epithelia were prepared as described herein. In vector transduction experiments, the cells were transduced with either Ad-NF-κB-Luc alone or with both Ad-NF-κB-Luc and Ad-MD-2 two days before performing experimental interventions. The vectors were formulated in 5 mM EGTA and applied to the apical surface (50 MOI) of the cells for 2 hours in a 100 μl volume as described previously to access receptors (Wang et al., 2000). The vector solution was removed, and the cells were transferred to another multiwell culture dish with fresh culture medium. On the experimental day, LOS±specific endotoxin-binding proteins as indicated in the individual figure legends were applied in 50 μl to the apical or basolateral side of the cells as noted. Control groups received PBS (negative control) or IL-1β (100 ng/ml, applied apically and basolaterally as positive control). 18–24 hours later, the cells were disrupted in the 1× lysis buffer provided with the luciferase assay kit (Promega) to measure luciferase activity. In addition, some samples were prepared to isolate total RNA.

HEK Cell Activation Assay

HEK cells+/−TLR4 were obtained from Dr. Jesse Chow (Eisai Research Institute, Andover, Mass.) and were cultured as described (Yang et al., 2000; and Gioannini et al., 2003). For cell activation assays, cells were grown to confluency in 48 well plates. Epithelia were washed with warm PBS 2× and incubated overnight at 37° C., 5% $CO_2$, and 95% humidity in Hanks' balanced salts solution, 0.1 % human serum albumin with the supplements indicated in the legends to FIG. 8. Activation of HEK cells was assessed by measuring accumulation of extracellular IL-8 by ELISA as previously described (Denning et al., 1998).

Production of Recombinant MD-2 Protein

Recombinant MD-2 protein (rMD-2) was produced in baculovirus for application to airway epithelia. The human MD-2 cDNA was first sub-cloned into pGEM-T easy vector for transformation of E. coli JM109 and amplification. The DNA was then isolated, linearized, and inserted into pBAC11 (using NcoI and XhoI-sensitive restriction sites) for transfection into insect cells. A vector encoding a six-histidine ("poly-HIS") extension of the C-terminus was used. The DNA encoding MD-2 was sequenced in both directions to confirm the fidelity of the product. Sf9 cells were used for production and multiplication of virus containing pBAC11 plasmids. To maximize recombinant protein production, High Five (Invitrogen) cells were inoculated with recombinant virus in serum-free medium, incubated 24–48 hr and culture medium then collected for analysis. The presence of recombinant MD-2-(HIS)6 was determined by SDS-PAGE and immuno-blots of the culture medium, using an anti-His4 mAb (Qiagen). The culture medium was dialyzed against sterile Hanks' balanced salts solution buffered with 10 mM HEPES, pH 7.4 and supplemented with 0.1 % human serum albumin before use in bioassays.

Stimulation of Airway Epithelia with Pro-Inflammatory Products

Several agents were applied to human airway epithelia to investigate the regulation of MD-2 expression. PMA, TNF-α, and INF-γ were applied to the apical and basolateral surfaces at 100 ng/ml. Bacterial products including the NTHi membrane protein P6 (5 μml) and heat killed NTHi (Strain 12, ~100 bacteria per epithelial cell, Frick et al., 2000) were applied to the apical surface. Following an 18–24 hr stimulation, the cells were lysed and total RNA was extracted. Real-time PCR was conducted as described herein.

The present studies indicate that, under resting conditions, human airway epithelia are hypo-responsive to endotoxin stimulation. This observation was confirmed using LOS from two different Gram-negative bacterial species and several different presentations of LOS, including LOS-sCD14 that is active at pg/ml concentrations toward highly endotoxin responsive cells such as monocytes, macrophages and endothelial cells (Giardina et al., 2001; Gioanniniet al., 2002; and Iovine et al., 2002). However, airway epithelial cells are not generally hypo-responsive to all stimuli as shown by their robust responses to pro-inflammatory cytokines including IL-1β.

EXAMPLE 3

Endotoxin species with potent pro-inflammatory activity are typically hexa-acylated. That is, the lipid A region contains 6 covalently linked fatty acids, including 4 mol/mol of 3-OH fatty acids linked directly to the di-N-acetyglucosamine backbone of lipid A and 2 mol/mol non-hydroxylated fatty acids (NFA) that are linked to two of the four 3-OH fatty acids via an ester bond with the 3-OH group. The presence of the NFA is important for potent bioactivity of endotoxin. Either enzymatic release of the 2 NFA or disruption of the genes (htrB, msbB) encoding the two acyltransferases needed for their biosynthetic incorporation yields a tetra-acylated endotoxin derivative that lacks proinflammatory agonist activity and, instead, antagonizes wild-type endotoxin activity. Removal of just one of the two NFA (i.e. msbB mutant; penta-acylated endotoxin species) also typically exhibits markedly reduced agonist and partial antagonist activity toward human endotoxin-responsive cells.

Under-acylated endotoxin reacts normally with LBP, CD14 and MD-2 to produce an endotoxin-MD-2 complex that engages TLR4 without producing the changes in TLR4 needed for receptor and cell activation. The presence of an excess of under-acylated endotoxin-MD-2 complex (e.g., tetra- or penta-acylated endotoxin) competitively inhibits the activity of a wt endotoxin-MD-2 complex.

Figure 11:
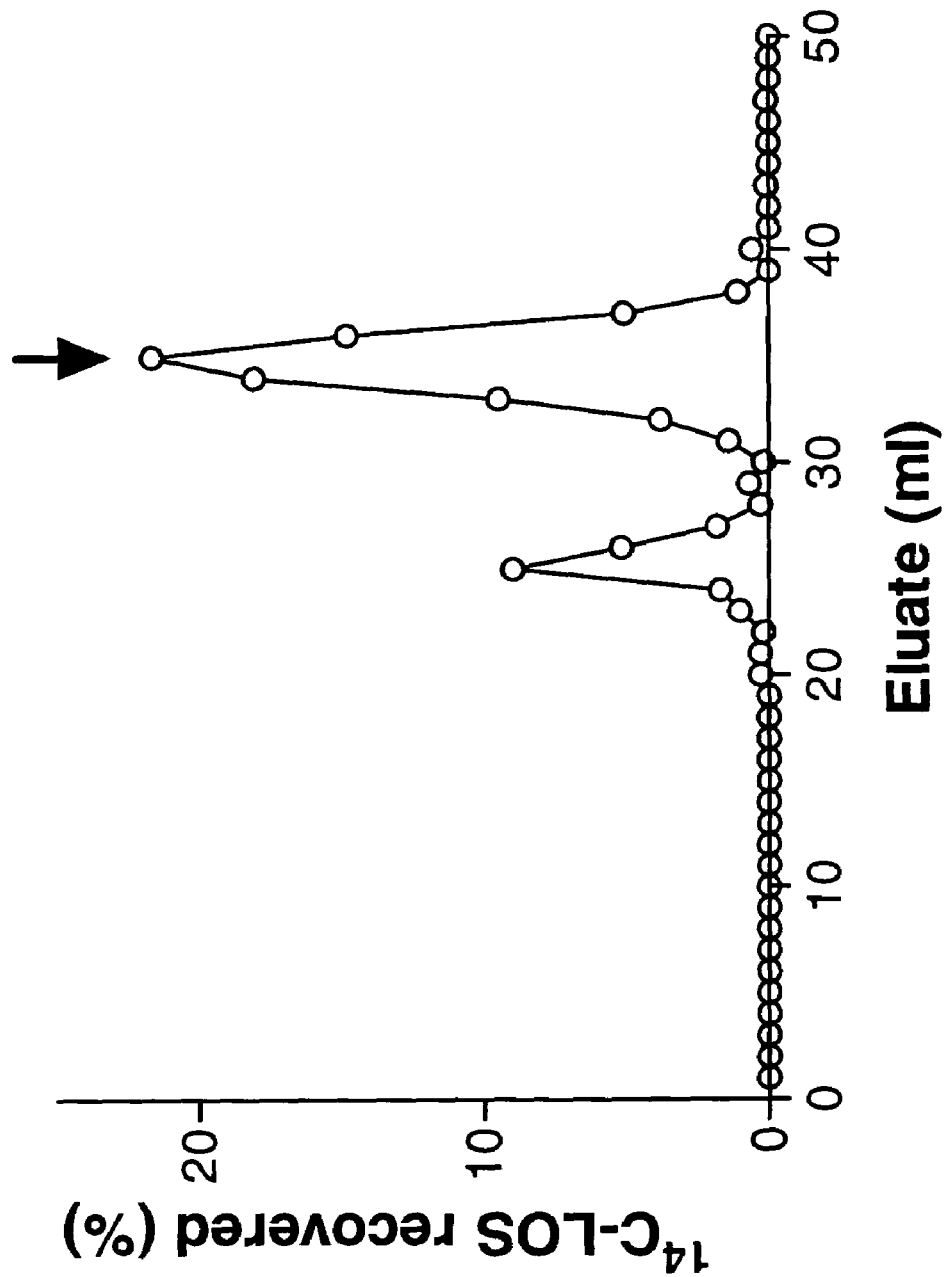
FIG. 11 depicts sephacryl S200 chromatography of $^{14}$C-msbB LOS aggregates (1 μg) pre-incubated with 100 ng LBP and 24 μg sCD14 for 15 min at 37° C. The arrow indicates elution of wt LOS-sCD14 complex.
Figure 12:
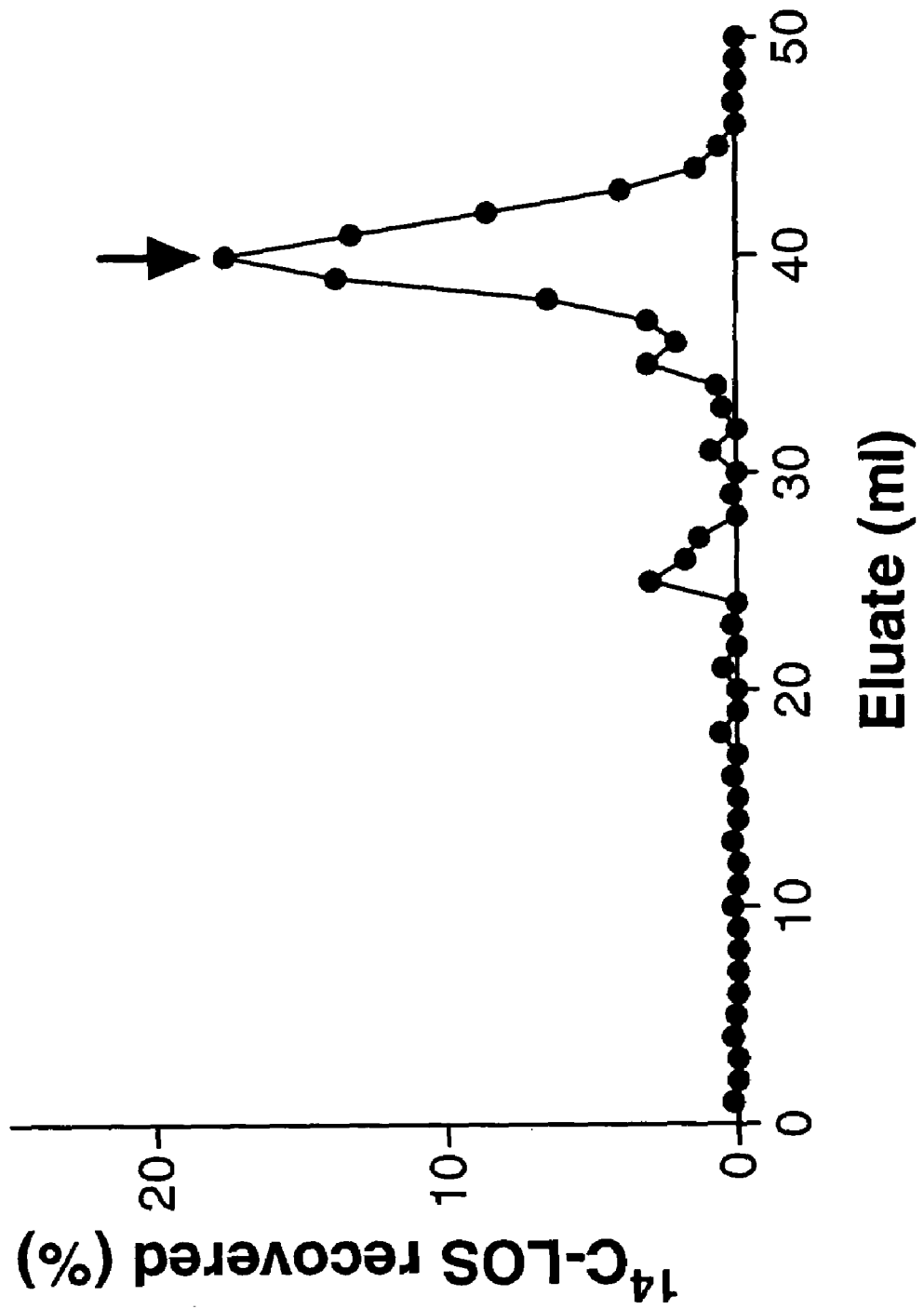
FIG. 12 depicts sephacryl S200 chromatography of $^{14}$C-msbB LOS-sCD14 (160 ng) pre-incubated with ~5 μg MD-2 for 15 min at 37° C. The arrow indicates elution of wt LOS-MD-2 complex.

An msbB mutant of Neisseria meningitidis serogroup B (NMB) was used to examine the effects of changes in acylation on TLR4 engagement and activation (see WO 97/19688). The parent strain was used for isolation of wild-type (wt; hexa-acylated) endotoxin (lipo-oligosaccharide; LOS). As described hereinabove in the previous Examples, metabolic labeling of the bacteria with $^3$H- or $^{14}$C-acetate was used to radiolabel the fatty acids of LOS during bacterial growth and de novo synthesis. Using the same methods described hereinabove in the previous Examples, production of predominantly hexa-acylated LOS by the wt strain (mol ratios of C12:0, 3-OH-12:0 and 3-OH-14:0=1.0/1.0/1.0) and of predominantly penta-acylated LOS by the msbB mutant strain (mol ratios=0.5/1.0/0.9) and reaction of each LOS species with LBP, sCD14 and MD-2 to form an endotoxin-MD-2 complex (see FIGS. 11 and 12 for formation and isolation of msbB LOS-sCD14 and msbB LOS-MD-2 complexes) was verified. The bioactivity of the wt and mutant endotoxin-MD-2 complexes was tested against HEK/TLR4 cells.

Figure 13:
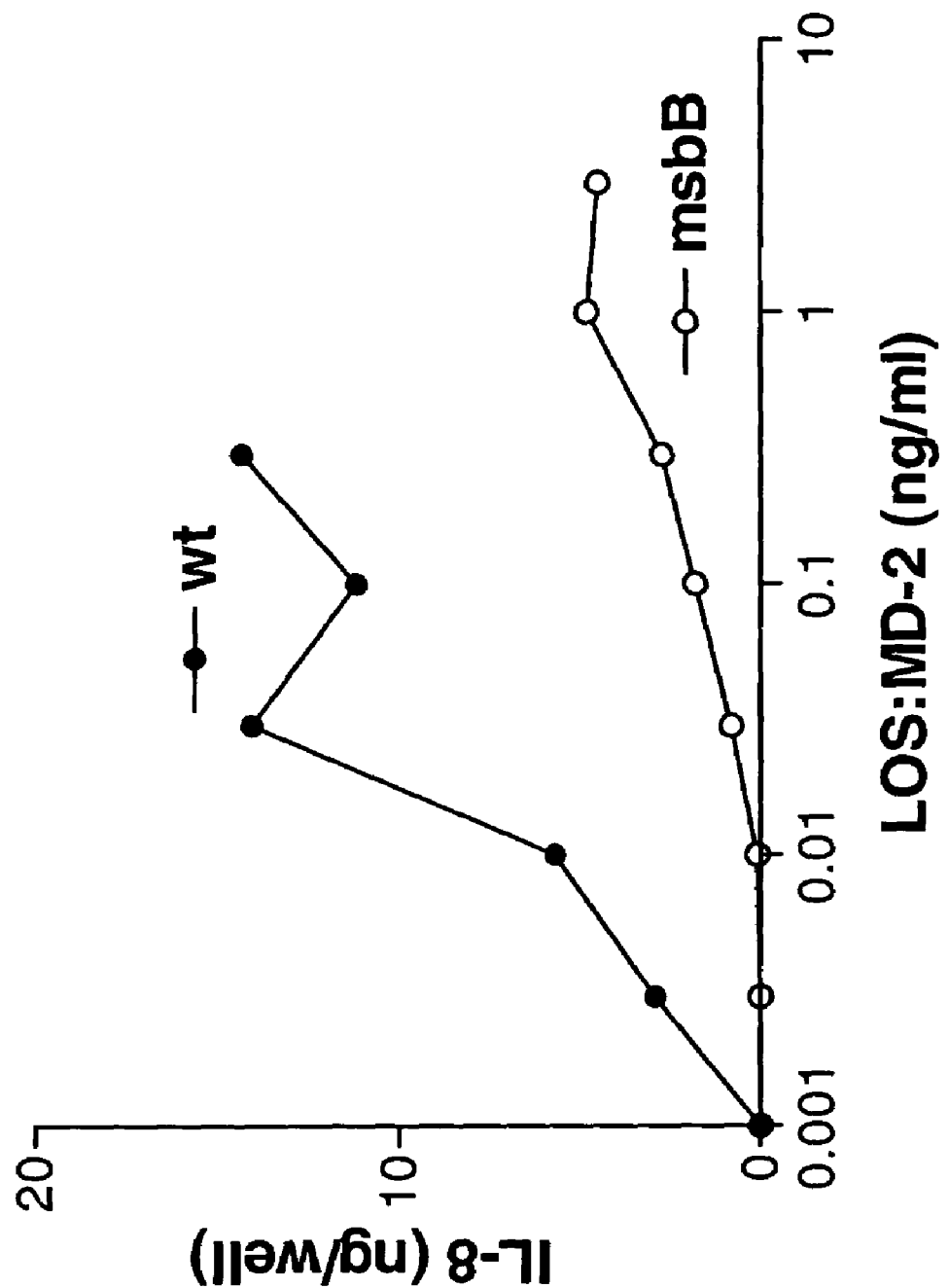
FIG. 13 depicts cell activation as measured by accumulation of extracellular IL-8, monitored by ELISA. HEK/TLR4 cells were incubated ON at 37° C. with increasing amounts of wt or mutant (msbB) LOS-MD-2, as indicated.
Figure 14:
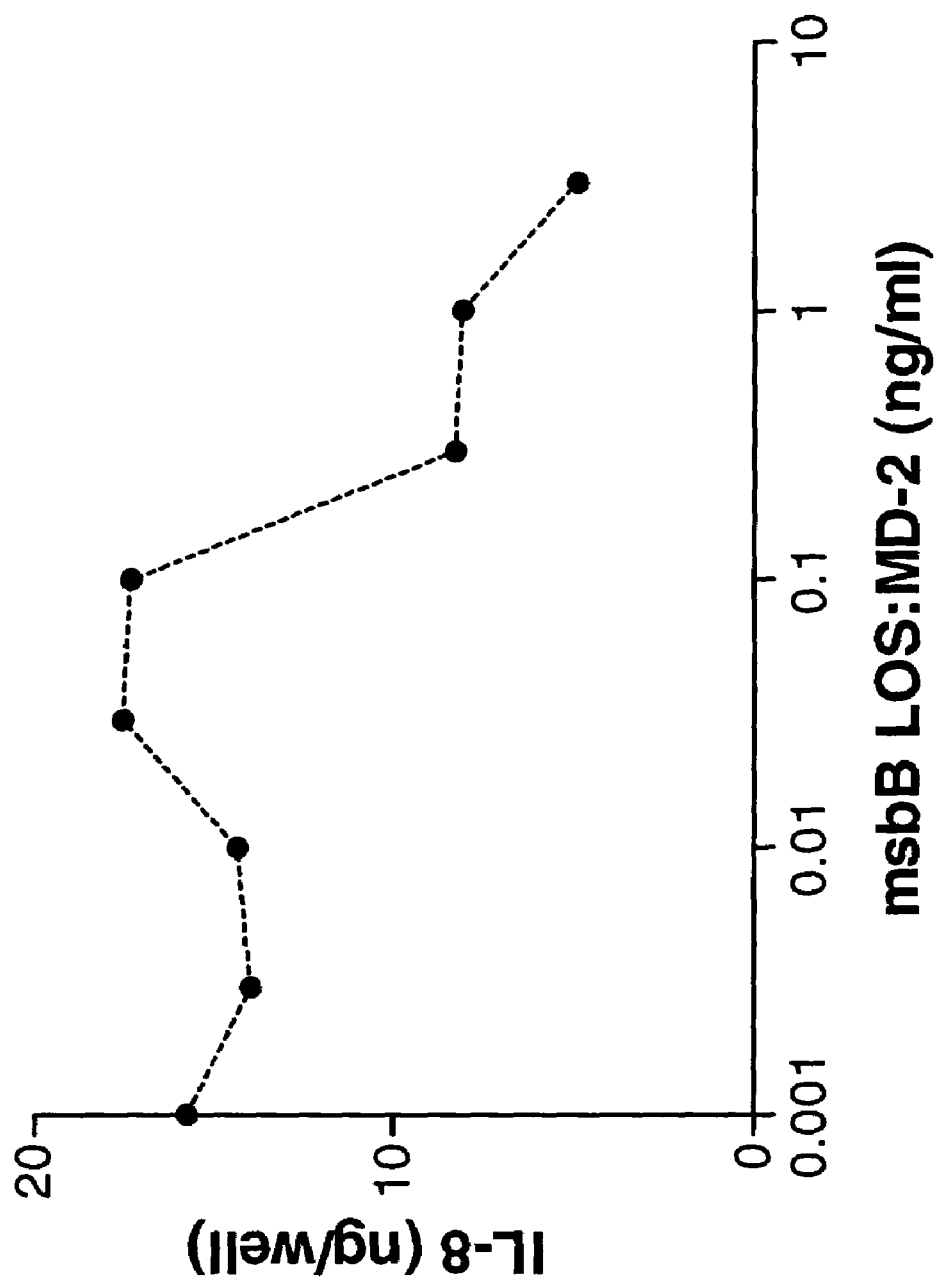
FIG. 14 depicts cell activation as measured by accumulation of extracellular IL-8, monitored by ELISA. HEK/TLR4 cells were incubated ON at 37° C. with 0.1 ng/ml of wt LOS-MD-2±increasing amounts of mutant msbB LOS-MD-2, as indicated.

As shown in FIG. 13, the activities of the endotoxin-MD-2 complexes differs markedly between the complex containing wt (hexa-acylated) LOS and that containing the mutant msbB (penta-acylated) LOS, with the complex containing the mutant LOS causing less cell activation. Moreover, addition of increasing amounts of the mutant msbB LOS-MD-2 complex significantly reduced cell activation by the wt LOS-MD-2 complex. Limited cell activation seen at higher doses of the msbB LOS-MD-2 complex closely resembles levels of cell activation produced by addition of these amounts of the msbB LOS-MD-2 complex alone (compare FIGS. 13 and 14) indicating that the mutant endotoxin-MD-2 complexes can efficiently compete with the wt endotoxin-MD-2 complex for interaction with cellular TLR4, and thus blunt endotoxin-induced cell activation.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

All publications, patents and patent applications cited herein are herein incorporated by reference.

DOCUMENTS CITED

Abreu et al., 2001. J Immunol 167; 1609.
Abreu et al., 2002. J Biol Chem 277; 20431.
Akashi et al., J Immunol 164, 3471–5. (2000).
Akashi et al., 2003. J Exp Med 198, 1035–42.
Anderson et al., 2000. Gene Ther 7; 1034.
Anderson, Curr Opin Immunol 12, 13-9. (2000).
Arbour et al., 2000. Nat Genet 25; 187.
Bals et al., 1998. J Clin Invest 102; 874.
Bandi et al., 2001. Am J Respir Crit Care Med 164; 2114.
Becker et al., 2000. J Biol Chem 275; 29731.
Beutler et al., Crit Care Med 29, S2–7. (2001).
Beutler et al., 2003. Nat Rev Immunol 3, 169.
Bustin, 2000. J Mol Endocrinol 25; 169.
da Silva et al., J Biol Chem 26, 26 (2001).
Denning et al., Infect Immun 66, 5777–84. (1998).
Douwes et al., 2003. Biological agents—recognition. In Modern Industrial Hygiene, Vol. 2. J. L. Perkins, ed. ACGIH, Cincinnati.
Frick et al., 2000. J Immunol 164; 4185.
Ganz, 2002. J Clin Invest 109; 693.
Garcia et al.,2001. FASEB J. 15; 1819.
Giardina et al., J Biol Chem 276, 5883–91. (2001).
Gioannini et al., 2002. J Biol Chem 277; 47818.
Gioannini et al., 2003. Isolation of an endotoxin: MD-2 complex that produces TLR4-dependent cell activation at pM concentrations. Submitted.
Gioannini et al., Journal of Endotoxin Research. In press (2003).
Gottar et al., 2002. Nature 24; 24.
Hailman et al., 1994. J Exp Med 179, 269–77.
Harder et al., 1997. Nature 387; 861.
Harder et al., 2000. Am J Respir Cell Mol Biol 22; 714.
Harder et al., 2001. J Biol Chem 276; 5707.
Hoffmann et al., 1999. Science 284; 1313.
Inzana et al., 1997. Infect Immun 65; 4675.
Iovine et al., J Biol Chem 277, 7970–8. (2002).
Janeway et al., 2002. Annu Rev Immunol 20; 197.
Jia et al., 2001. Gene 263; 211.
Jiang et al., J Immunol 165, 3541–4. (2000).
Karp et al., 2002. Methods Mol Biol 188; 115.
Kawasaki et al., J Endotoxin Res 7, 232–6 (2001).
Kawasaki et al., J Immunol 170, 413–20 (2003).
Lamping et al., J Clin Invest 101, 2065–71 (1998).
Latz et al., 2002. J Biol Chem. 277, 47834.
Lemaitre et al., 1996. Cell 86, 973.
Lerman et al., 1979. Pediatrics 64; 287.
Liu et al., 1998. Gene 222; 237.
Malley et al., 2003. Proc Natl Acad Sci USA 100; 1966.
Mathews et al., 1999. Infect Immun 67; 2740.
McCray et al., 1997. Am J Respir Cell Mol Biol 16; 343.
McCray et al., 1997. Hum.Gene Ther. 8; 1087.
McNamara et al., 1999. Exp Eye Res 69; 483.
Means et al., Cytokine Growth Factor Rev 11, 219–32. (2000).
Medzhitov et al., 1997. Nature 388; 394.
Medzhitov et al., Curr Opin Immunol 10, 12-5. (1998).
Medzhitov et al., 2000. Immunol Rev 173; 89.
Miyake, Int Immunopharmacol 3, 119–28 (2003).
Mueller-Anneling et al., 2003. Measurement of endotoxin in ambient PM10 in Southern California. Submitted.
Mullen et al., 2003. Proc Natl Acad Sci USA 100, 3919–24.
Munford et al., 1992. J Immunol Methods 148, 115–20.
Muroi et al., 2002. J Biol Chem 277, 42372–9.
Muroi et al., Infect Immun 70, 3546–50 (2002).
Nagai et al., Nat Immunol 3, 667–72 (2002).
Ohnishi et al., J Immunol 167, 3354–9. (2001).
ONeil et al., 1999. J Immunol 163; 6718.
Re et al., J Biol Chem 277, 23427–32 (2002).
Re et al., Journal of Immunology, 171, 5272–5276 (2003).
Reynolds, 1997. Integrated host defense against infections. In The Lung. R. G.
Crystal, J. B. West, E. R. Weibel, and P. J. Barnes, eds. Raven Press,Ltd., New York, N.Y., p. 2353.
Schroder et al., 1999. Int J Biochem Cell Biol 31; 645.
Schromm et al., J Exp Med 194, 79–88. (2001).
Schutt, Int J Biochem Cell Biol 31, 545–9 (1999).
Schutte et al., 2002. Annu Rev Physiol 64; 709.
Schutte et al., 2002. Proc Natl Acad Sci 99; 2129.
Shimazu et al., J Exp Med 189, 1777–82. (1999).
Singh et al., 1998. Proc Natl Acad Sci USA 95; 14961.
Smith et al., 1989. Acta Paediatr Scand Suppl 363; 31.
Takeda et al., 2003. Cell Microbiol 5, 143–53.
Tapping et al., 1997. J Biol Chem 272, 23157–64.
Tauszig et al., 2000. Proc Natl Acad Sci USA 97; 10520.
Thomas et al., 2002. FEBS Lett 531, 184–8.
Tsutsumi-Ishii et al., 2003. J Immunol 170; 4226.
Ulevitch, Immunol Res 21, 49–54. (2000).
Ulevitch et al., 1999. Curr Opin Immunol 11, 19–22.
Viriyakosol et al., J Biol Chem 276, 38044–38051. (2001).
Visintin et al., Proc Natl Acad Sci USA 98, 12156–61 (2001).
Visintin et al., 2003. "Lysines 128 and 132 Enable LPS Binding to MD-2, Leading to Toll-like Receptor 4 Aggregation and Signal Transduction., J Biol Chem.
Wang et al., 2000. Am J Respir Cell Mol Biol 22; 129.
Wang et al., 2002. J Immunol 168; 810.
Weiss, Biochemical Society Transactions (2003).
Yang et al., J Biol Chem 275, 20861–6. (2000).

Yu et al., 1996. J Biol Chem 271, 4100–5.
Zasloff, 2002. Nature 415; 389.

What is claimed is:

1. A purified complex consisting of one molecule of endotoxin bound to one molecule of MD-2.
2. The complex of claim 1, wherein the endotoxin is a wild-type endotoxin.
3. The complex of claim 1, wherein the endotoxin is a gram-negative bacterial endotoxin.
4. The complex of claim 3, wherein the gram-negative bacterium is a *Neisseria, Escherichia, Pseudomonas, Haemophilus, Salmonella,* or *Fraricisella* bacterium.
5. The complex of claim 4, wherein the gram-negative bacterium is *Neisseria meningitidis, Escherichia coil, Pseudomonas aeruginosa, Haemophilus influenzae, Salmonella typhimurium,* or *Francisella tularensis.*
6. The complex of claim 1 having a molecular weight of about 25,000.
7. The complex of claim 1, wherein the complex is soluble in water.
8. The complex of claim 1, wherein the complex binds to TLR4.
9. The complex of claim 1, wherein the complex produces TLR4-dependent activation of cells.
10. The purified complex of claim 9, wherein the complex is administered at a concentration of less than 1 nM produces a half maximal TLR4-dependent activation of cells.
11. The complex of claim 9, wherein the complex is administered at a concentration of less than 30 pM produces a half maximal TLR4-dependent activation of cells.
12. A purified complex comprising endotoxin bound to MD-2, wherein the endotoxin is selected from the group consisting of hexa-acylated endotoxin, under-acylated endotoxin, penta-acylated endotoxin and tetra-acylated endotoxin.
13. The complex of claim 12, wherein the purified complex consists of one molecule of endotoxin bound to one molecule of MD-2.
14. The complex of claim 12, wherein the endotoxin is a tetra-acylated endotoxin.
15. The complex of claim 12, wherein the endotoxin is a penta-acylated endotoxin.
16. The complex of claim 12, wherein the complex produces less TLR4-dependent activation of cells when the endotoxin is under-acylated as compared to a complex comprising an endotoxin that is hexa-acylated.
17. The complex of claim 12, wherein the endotoxin is under-acylated.
18. The complex of claim 12, wherein the endotoxin is hexa-acylated.
19. A composition comprising a purified complex comprising endotoxin bound to MD-2, wherein the endotoxin is selected from the group consisting of hexa-acylated endotoxin, under-acylated endotoxin, penta-acylated endotoxin and tetra-acylated endotoxin and a pharmaceutically acceptable carrier.
20. The composition of claim 19, wherein the endotoxin is hexa-acylated.
21. The composition of claim 19, wherein the endotoxin is under-acylated.
22. The composition of claim 19, wherein the endotoxin is a tetra-acylated endotoxin.
23. The composition of claim 19, wherein the endotoxin is a penta-acylated endotoxin.
24. A composition consisting of the purified complex of claim 1 and a pharmaceutically acceptable carrier.

* * * * *

UNITED STATES PATENT AND TRADEMARK OFFICE
CERTIFICATE OF CORRECTION

PATENT NO. : 7,164,008 B2
APPLICATION NO. : 10/715876
DATED : January 16, 2007
INVENTOR(S) : Jerrold P. Weiss et al.

It is certified that error appears in the above-identified patent and that said Letters Patent is hereby corrected as shown below:

In column 33, line 12, in Claim 4, delete "Fraricisella" and insert --Francisella--.

In column 33, line 14, in Claim 5, delete "coil" and insert --coli--.

Signed and Sealed this

Eighteenth Day of September, 2007

JON W. DUDAS
*Director of the United States Patent and Trademark Office*